(12) United States Patent
Kirschman

(10) Patent No.: US 7,717,943 B2
(45) Date of Patent: *May 18, 2010

(54) CAPLESS MULTIAXIAL SCREW AND SPINAL FIXATION ASSEMBLY AND METHOD

(75) Inventor: David Louis Kirschman, Dayton, OH (US)

(73) Assignee: X-spine Systems, Inc., Miamisburg, OH (US)

(*) Notice: Subject to any disclaimer, the term of this patent is extended or adjusted under 35 U.S.C. 154(b) by 1005 days.

This patent is subject to a terminal disclaimer.

(21) Appl. No.: 11/193,523

(22) Filed: Jul. 29, 2005

(65) Prior Publication Data

US 2007/0043357 A1    Feb. 22, 2007

(51) Int. Cl.
*A61B 17/70* (2006.01)

(52) U.S. Cl. .............. 606/269; 606/266; 606/267; 606/264; 606/265; 606/300

(58) Field of Classification Search .......... 606/246, 606/264, 265, 267, 268, 269, 270, 271, 272, 606/273, 274, 275, 279, 266, 300, 301, 302, 606/303, 304, 305, 306, 307, 308, 309, 310, 606/311, 312, 313, 314, 315, 316, 317, 318, 606/319, 320, 54, 55, 56, 57, 58, 59, 250–263; 623/17.11

See application file for complete search history.

(56) References Cited

U.S. PATENT DOCUMENTS

| | | |
|---|---|---|
| 483,342 A | 9/1892 | Bolte |
| 900,717 A | 10/1908 | Feaster |
| 2,344,381 A | 3/1944 | Young |
| 3,019,504 A | 2/1962 | Castagliuolo |
| 3,648,691 A | 3/1972 | Lumb et al. |
| 3,752,203 A | 8/1973 | Hill, Jr. |
| 3,851,601 A | 12/1974 | Davis |
| 3,875,936 A | 4/1975 | Volz |
| 4,011,602 A | 3/1977 | Rybicki et al. |
| 4,085,744 A | 4/1978 | Lewis et al. |
| 4,269,178 A | 5/1981 | Keene |
| 4,289,124 A | 9/1981 | Zickel |
| 4,294,300 A | 10/1981 | Bouwman |
| 4,309,139 A | 1/1982 | Nakae |
| 4,411,259 A | 10/1983 | Drummond |
| 4,604,995 A | 8/1986 | Stephens et al. |
| 4,611,580 A | 9/1986 | Wu |

(Continued)

FOREIGN PATENT DOCUMENTS

DE        3219575        12/1983

(Continued)

OTHER PUBLICATIONS

Expedium Spine System, DePuy Spine, Raynham, MA 02767.

*Primary Examiner*—Eduardo C Robert
*Assistant Examiner*—Jan Christopher Merene
(74) *Attorney, Agent, or Firm*—Jacox, Meckstroth & Jenkins

(57) ABSTRACT

A spinal fixation assembly and capless multi-axial screw system and method are shown. The assembly comprises a receiver having a rotary lock which in one embodiment includes a plurality of channels which urge and lock the elongated member to the screw using a bayonet type connection.

59 Claims, 9 Drawing Sheets

U.S. PATENT DOCUMENTS

| | | |
|---|---|---|
| 4,611,581 A | 9/1986 | Steffee |
| 4,641,636 A | 2/1987 | Cotrel |
| 4,648,388 A | 3/1987 | Steffee |
| 4,653,481 A | 3/1987 | Howland et al. |
| 4,655,199 A | 4/1987 | Steffee |
| 4,658,809 A | 4/1987 | Ulrich et al. |
| 4,696,290 A | 9/1987 | Steffee |
| 4,719,905 A | 1/1988 | Steffee |
| 4,763,644 A | 8/1988 | Webb |
| 4,771,767 A | 9/1988 | Steffee |
| 4,805,602 A | 2/1989 | Puno et al. |
| 4,815,453 A | 3/1989 | Cotrel |
| 4,887,595 A | 12/1989 | Heinig et al. |
| 4,887,596 A | 12/1989 | Sherman |
| 4,913,134 A | 4/1990 | Luque |
| 4,946,458 A | 8/1990 | Harms et al. |
| 4,950,269 A | 8/1990 | Gaines, Jr. |
| 5,005,562 A | 4/1991 | Cotrel |
| 5,024,213 A | 6/1991 | Asher et al. |
| 5,042,982 A | 8/1991 | Harms et al. |
| 5,067,955 A | 11/1991 | Cotrel |
| 5,084,049 A | 1/1992 | Asher et al. |
| 5,092,867 A | 3/1992 | Harms et al. |
| 5,113,685 A | 5/1992 | Asher et al. |
| 5,120,171 A | 6/1992 | Lasner |
| 5,127,912 A | 7/1992 | Ray et al. |
| 5,129,900 A | 7/1992 | Asher et al. |
| 5,176,680 A | 1/1993 | Vignaud et al. |
| 5,183,359 A | 2/1993 | Barth |
| 5,190,543 A | 3/1993 | Schläpfer |
| 5,207,678 A | 5/1993 | Harms et al. |
| 5,246,303 A | 9/1993 | Trilla et al. |
| 5,257,993 A | 11/1993 | Asher et al. |
| 5,261,913 A | 11/1993 | Marnay |
| 5,312,402 A * | 5/1994 | Schlapfer et al. ............... 606/53 |
| 5,346,493 A | 9/1994 | Stahurski et al. |
| 5,360,431 A | 11/1994 | Puno et al. |
| 5,380,325 A | 1/1995 | Lahille et al. |
| 5,466,237 A | 11/1995 | Byrd, III et al. |
| 5,474,555 A | 12/1995 | Puno et al. |
| 5,520,689 A * | 5/1996 | Schlapfer et al. ............. 606/270 |
| 5,534,001 A | 7/1996 | Schlapfer et al. |
| 5,549,608 A | 8/1996 | Errico et al. |
| 5,562,663 A | 10/1996 | Wisnewski et al. |
| 5,603,714 A * | 2/1997 | Kaneda et al. ............... 606/272 |
| 5,609,593 A | 3/1997 | Errico et al. |
| 5,624,442 A | 4/1997 | Mellinger et al. |
| 5,647,873 A | 7/1997 | Errico et al. |
| 5,667,508 A | 9/1997 | Errico et al. |
| 5,669,911 A | 9/1997 | Errico et al. |
| 5,690,630 A | 11/1997 | Errico et al. |
| 5,797,911 A | 8/1998 | Sherman et al. |
| 5,817,094 A | 10/1998 | Errico et al. |
| 5,879,350 A | 3/1999 | Sherman et al. |
| 5,882,350 A | 3/1999 | Ralph et al. |
| 5,885,286 A | 3/1999 | Sherman et al. |
| 5,891,145 A | 4/1999 | Morrison et al. |
| 5,954,725 A | 9/1999 | Sherman et al. |
| 6,010,503 A | 1/2000 | Richelsoph et al. |
| 6,063,090 A | 5/2000 | Schlapfer |
| 6,077,262 A | 6/2000 | Schlapfer et al. |
| 6,090,111 A | 7/2000 | Nichols |
| 6,113,601 A | 9/2000 | Tatar |
| 6,132,432 A | 10/2000 | Richelsoph |
| 6,235,033 B1 | 5/2001 | Brace et al. |
| 6,280,442 B1 | 8/2001 | Barker et al. |
| 6,302,888 B1 | 10/2001 | Mellinger et al. |
| RE37,665 E | 4/2002 | Ralph et al. |
| 6,371,957 B1 | 4/2002 | Amrein et al. |
| 6,402,752 B2 | 6/2002 | Schaffler-Wachter et al. |
| 6,451,021 B1 | 9/2002 | Ralph et al. |
| 6,475,218 B2 | 11/2002 | Gournay et al. |
| 6,488,681 B2 | 12/2002 | Martin et al. |
| 6,623,485 B2 | 9/2003 | Doubler et al. |
| 6,626,908 B2 | 9/2003 | Cooper et al. |
| 6,652,526 B1 | 11/2003 | Arafiles |
| 6,660,004 B2 | 12/2003 | Barker et al. |
| 6,716,214 B1 | 4/2004 | Jackson |
| 6,730,089 B2 | 5/2004 | Jackson |
| 6,730,093 B2 | 5/2004 | Saint Martin |
| 6,755,829 B1 | 6/2004 | Bono et al. |
| 6,786,903 B2 | 9/2004 | Lin |
| 6,793,657 B2 | 9/2004 | Lee et al. |
| 6,802,844 B2 | 10/2004 | Ferree |
| 6,827,719 B2 | 12/2004 | Ralph et al. |
| 6,840,940 B2 | 1/2005 | Ralph et al. |
| 6,843,791 B2 | 1/2005 | Serhan |
| 6,858,030 B2 | 2/2005 | Martin et al. |
| 6,863,464 B1 | 3/2005 | Niklaus |
| 6,869,433 B2 | 3/2005 | Glascott |
| 6,896,677 B1 | 5/2005 | Lin |
| 7,022,122 B2 * | 4/2006 | Amrein et al. ............... 606/266 |
| 7,081,117 B2 | 7/2006 | Bono et al. |
| 7,083,621 B2 * | 8/2006 | Shaolian et al. ............ 606/86 A |
| 7,125,426 B2 | 10/2006 | Moumene et al. |
| 7,141,051 B2 | 11/2006 | Janowski et al. |
| 7,261,715 B2 | 8/2007 | Rezach et al. |
| 7,291,151 B2 | 11/2007 | Alvarez |
| 7,294,128 B2 | 11/2007 | Alleyne et al. |
| 7,322,981 B2 | 1/2008 | Jackson |
| 7,338,491 B2 | 3/2008 | Baker et al. |
| 7,604,655 B2 * | 10/2009 | Warnick ..................... 606/265 |
| 2002/0013585 A1 | 1/2002 | Gournay et al. |
| 2002/0082601 A1 * | 6/2002 | Toyama et al. ................ 606/61 |
| 2002/0091386 A1 | 7/2002 | Martin et al. |
| 2002/0111626 A1 | 8/2002 | Ralph et al. |
| 2002/0120272 A1 | 8/2002 | Yuan et al. |
| 2002/0133154 A1 | 9/2002 | Saint Martin |
| 2002/0133158 A1 | 9/2002 | Saint Martin |
| 2002/0143341 A1 | 10/2002 | Biedermann |
| 2002/0183748 A1 | 12/2002 | Martin et al. |
| 2003/0032957 A1 | 2/2003 | McKinley |
| 2003/0073996 A1 | 4/2003 | Doubler et al. |
| 2003/0078583 A1 | 4/2003 | Biedermann et al. |
| 2003/0187433 A1 | 10/2003 | Lin |
| 2003/0187434 A1 | 10/2003 | Lin |
| 2003/0199873 A1 * | 10/2003 | Richelsoph .................. 606/61 |
| 2004/0039383 A1 | 2/2004 | Jackson |
| 2004/0039384 A1 * | 2/2004 | Boehm et al. ................. 606/61 |
| 2004/0049190 A1 | 3/2004 | Biedermann |
| 2004/0097933 A1 | 5/2004 | Lourdel et al. |
| 2004/0116929 A1 | 6/2004 | Barker et al. |
| 2004/0127896 A1 | 7/2004 | Lombardo et al. |
| 2004/0138662 A1 | 7/2004 | Landry et al. |
| 2004/0153068 A1 | 8/2004 | Janowski et al. |
| 2004/0172020 A1 * | 9/2004 | Beaurain et al. ............. 606/61 |
| 2004/0172022 A1 | 9/2004 | Landry et al. |
| 2004/0236330 A1 | 11/2004 | Purcell et al. |
| 2004/0267264 A1 | 12/2004 | Konieczynski et al. |
| 2005/0033296 A1 | 2/2005 | Bono et al. |
| 2005/0049589 A1 | 3/2005 | Jackson |
| 2005/0096653 A1 | 5/2005 | Doubler et al. |
| 2005/0113830 A1 | 5/2005 | Rezach et al. |
| 2005/0131410 A1 | 6/2005 | Lin |
| 2005/0177154 A1 | 8/2005 | Moumene et al. |
| 2005/0177157 A1 | 8/2005 | Jahng |
| 2005/0182400 A1 | 8/2005 | White |
| 2005/0187548 A1 | 8/2005 | Butler et al. |
| 2005/0192570 A1 | 9/2005 | Jackson |
| 2005/0192571 A1 | 9/2005 | Abdelgany |
| 2005/0192573 A1 | 9/2005 | Abdelgany et al. |
| 2005/0203515 A1 | 9/2005 | Doherty et al. |
| 2005/0203516 A1 * | 9/2005 | Biedermann et al. .......... 606/61 |
| 2005/0203519 A1 | 9/2005 | Harms et al. |

| | | |
|---|---|---|
| 2005/0215998 A1 | 9/2005 | Donath |
| 2005/0215999 A1 | 9/2005 | Birkmeyer et al. |
| 2005/0216003 A1 | 9/2005 | Biedermann et al. |
| 2005/0216004 A1 | 9/2005 | Schwab |
| 2005/0222570 A1 | 10/2005 | Jackson |
| 2005/0261687 A1 | 11/2005 | Garamszegi et al. |
| 2006/0025771 A1 | 2/2006 | Jackson |
| 2006/0069391 A1 | 3/2006 | Jackson |
| 2006/0084982 A1 | 4/2006 | Kim |
| 2006/0084984 A1 | 4/2006 | Kim |
| 2006/0084987 A1 | 4/2006 | Kim |
| 2006/0089644 A1 | 4/2006 | Felix |
| 2006/0100621 A1 | 5/2006 | Jackson |
| 2006/0100622 A1 | 5/2006 | Jackson |
| 2006/0111712 A1 | 5/2006 | Jackson |
| 2006/0111715 A1 | 5/2006 | Jackson |
| 2006/0129147 A1 | 6/2006 | Biedermann et al. |
| 2006/0129149 A1 | 6/2006 | Iott et al. |
| 2006/0142760 A1 | 6/2006 | McDonnell |
| 2006/0155278 A1* | 7/2006 | Warnick ............... 606/61 |
| 2006/0161152 A1 | 7/2006 | Ensign et al. |
| 2006/0161153 A1* | 7/2006 | Hawkes et al. ......... 606/61 |
| 2006/0173456 A1 | 8/2006 | Hawkes et al. |
| 2006/0195086 A1 | 8/2006 | Sybert |
| 2006/0200128 A1 | 9/2006 | Mueller |
| 2006/0217716 A1 | 9/2006 | Baker et al. |
| 2006/0229615 A1* | 10/2006 | Abdou ................. 606/61 |
| 2006/0235392 A1 | 10/2006 | Hammer et al. |
| 2006/0235393 A1 | 10/2006 | Bono et al. |
| 2006/0241603 A1 | 10/2006 | Jackson |
| 2006/0264933 A1 | 11/2006 | Baker et al. |
| 2006/0276792 A1 | 12/2006 | Ensign et al. |
| 2006/0293659 A1 | 12/2006 | Alvarez |
| 2006/0293664 A1 | 12/2006 | Schumacher |
| 2007/0043359 A1 | 2/2007 | Altarac et al. |
| 2007/0055242 A1 | 3/2007 | Bailly |
| 2007/0093827 A1* | 4/2007 | Warnick ............... 606/61 |
| 2007/0093831 A1 | 4/2007 | Abdelgany et al. |
| 2007/0093832 A1 | 4/2007 | Abdelgany |
| 2007/0100341 A1 | 5/2007 | Reglos et al. |
| 2007/0123862 A1 | 5/2007 | Warnick |
| 2007/0123867 A1* | 5/2007 | Kirschman ............ 606/61 |
| 2007/0162008 A1 | 7/2007 | Cline, Jr. et al. |
| 2007/0167949 A1 | 7/2007 | Altarac et al. |
| 2007/0239159 A1 | 10/2007 | Altarac et al. |
| 2007/0293861 A1 | 12/2007 | Rezach et al. |
| 2008/0039839 A1 | 2/2008 | Songer et al. |
| 2008/0039840 A1 | 2/2008 | Songer et al. |
| 2008/0045956 A1 | 2/2008 | Songer et al. |
| 2008/0071277 A1 | 3/2008 | Warnick |
| 2008/0097441 A1 | 4/2008 | Hayes et al. |
| 2008/0097457 A1 | 4/2008 | Warnick |
| 2008/0167689 A1* | 7/2008 | Matthis et al. ......... 606/305 |

FOREIGN PATENT DOCUMENTS

| | | |
|---|---|---|
| DE | 3639810 | 5/1988 |
| DE | 3711013 | 6/1988 |
| DE | 9403231 U1 | 4/1994 |
| EP | 0128058 | 12/1984 |
| EP | 0242705 | 10/1987 |
| EP | 0242708 | 10/1987 |
| EP | 1190678 A2 | 3/2002 |
| EP | 1210914 A1 | 5/2002 |
| EP | 1604617 A1 | 12/2005 |
| FR | 2615095 | 11/1988 |
| FR | 2624720 | 6/1989 |
| FR | 2706762 A1 | 12/1994 |
| FR | 2852815 A1 | 10/2004 |
| GB | 167228 | 7/1921 |
| GB | 2173104 | 10/1986 |
| WO | WO 8707134 | 12/1987 |
| WO | 01-52758 | 6/2001 |
| WO | WO/02/080788 * | 10/2002 .......... 606/270 |
| WO | 03086204 A2 | 4/2003 |
| WO | 2004103194 A1 | 5/2004 |
| WO | 2004089245 A2 | 10/2004 |
| WO | WO 2006/047555 | 5/2006 |
| WO | WO 2006/047707 | 5/2006 |
| WO | WO 2006/047711 | 5/2006 |

* cited by examiner

FIG-1
FIG-2
FIG-3
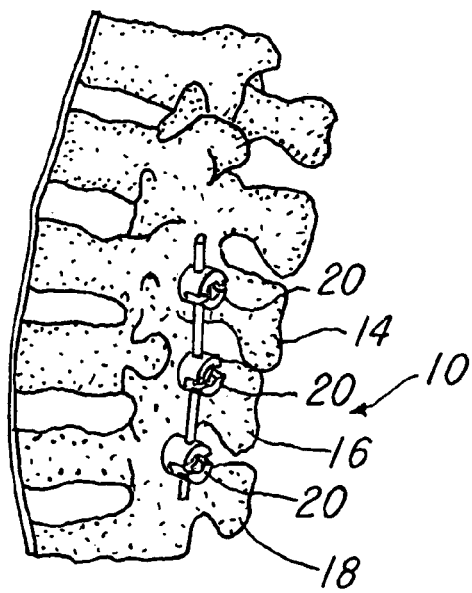
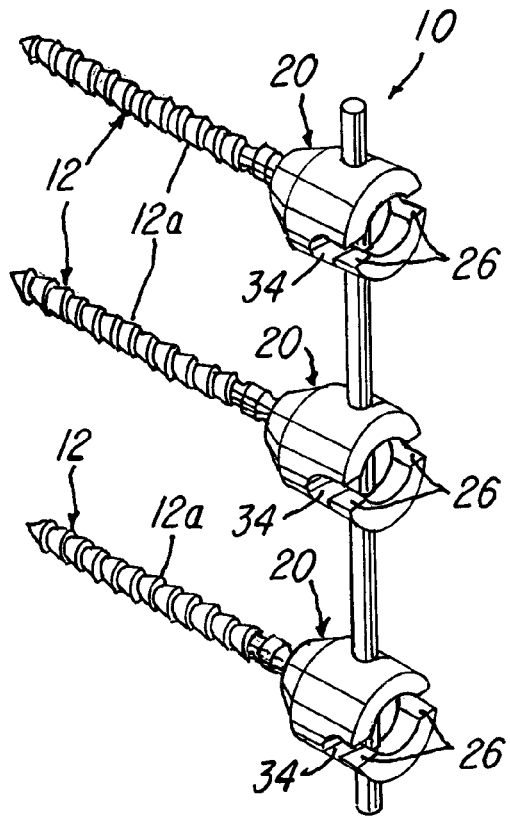
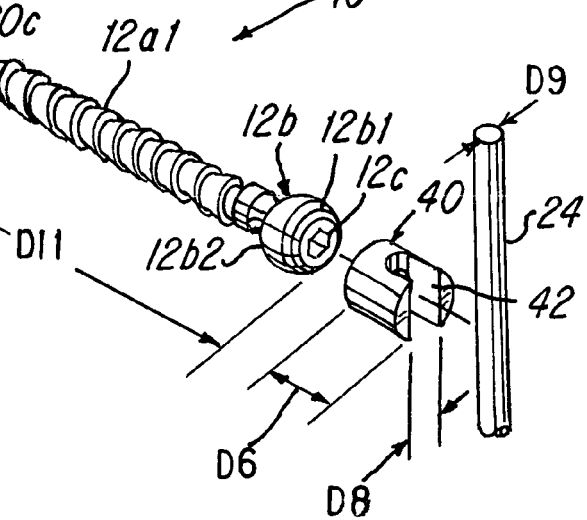

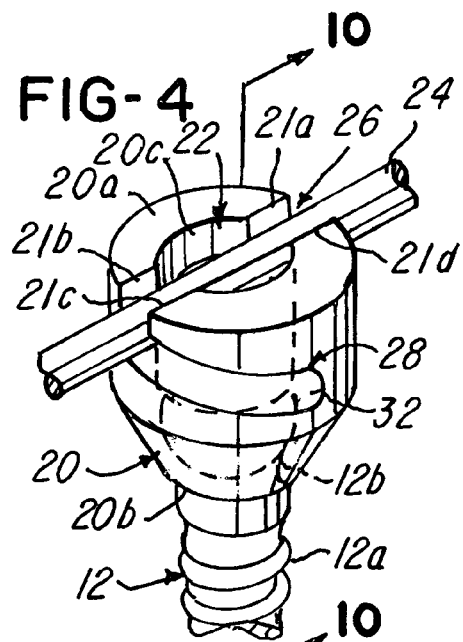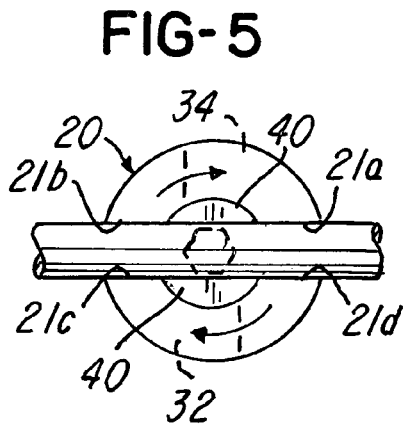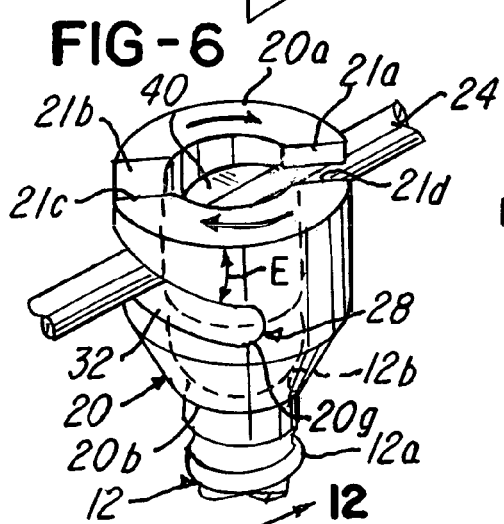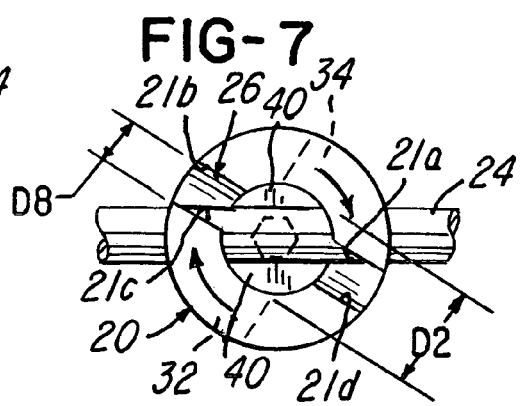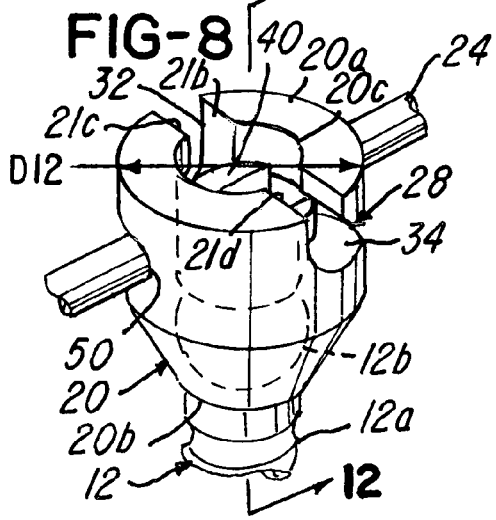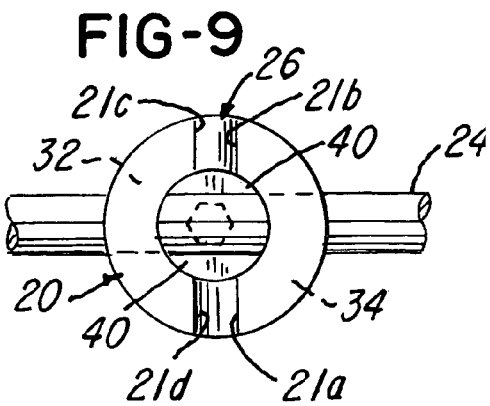

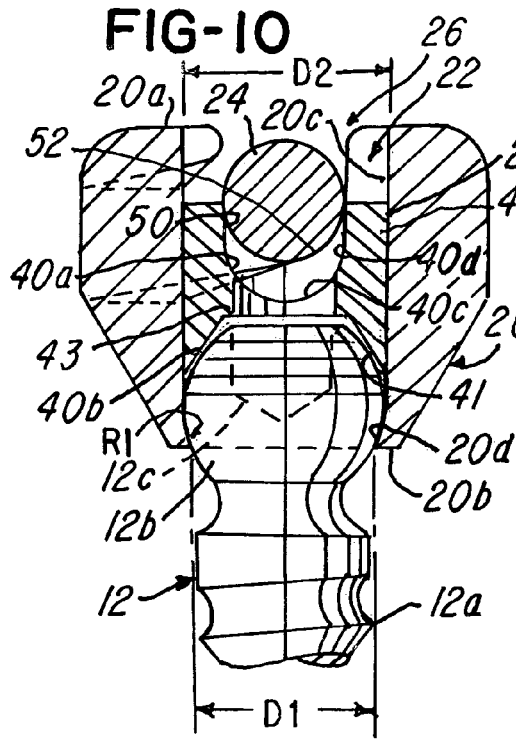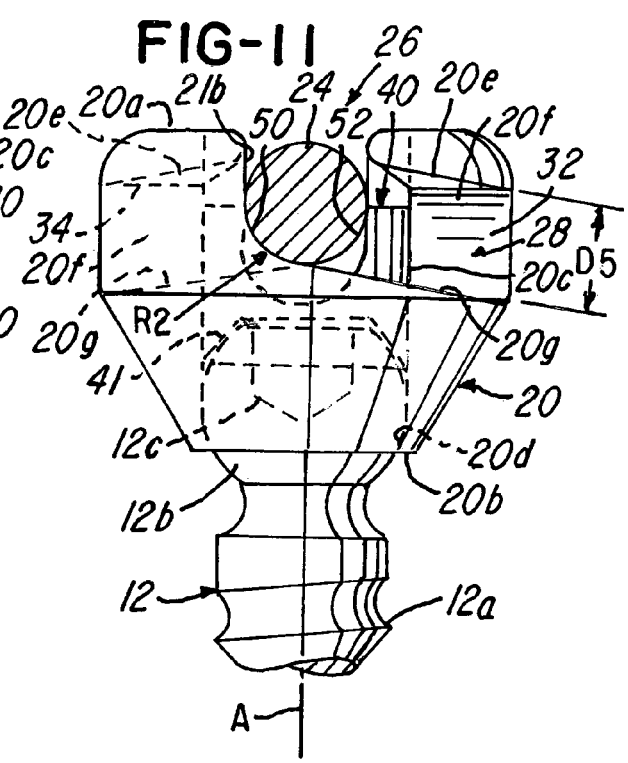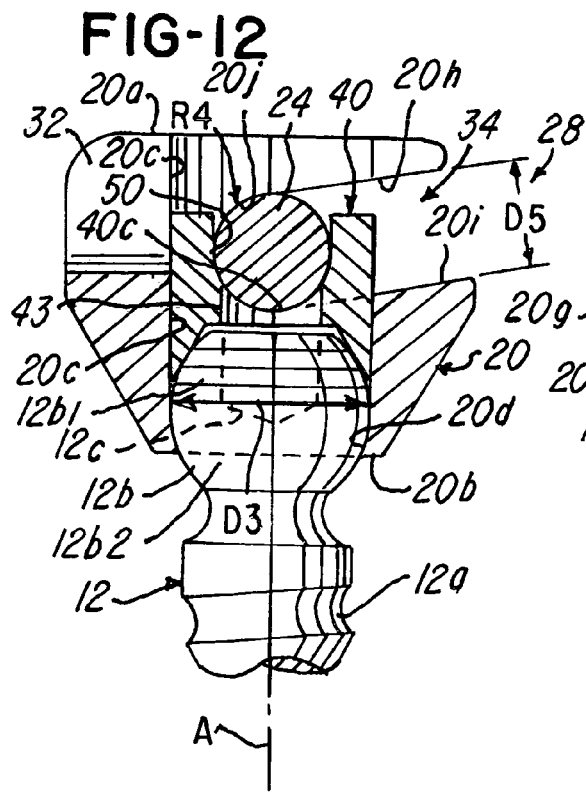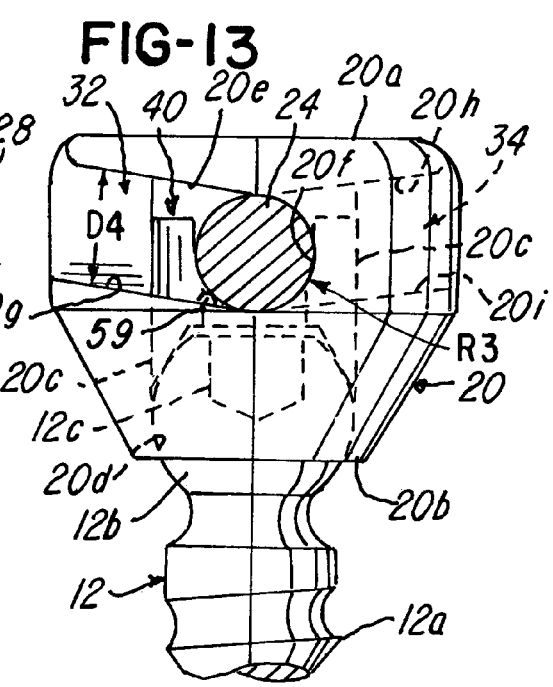

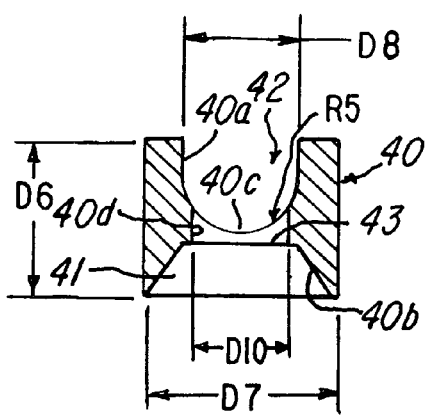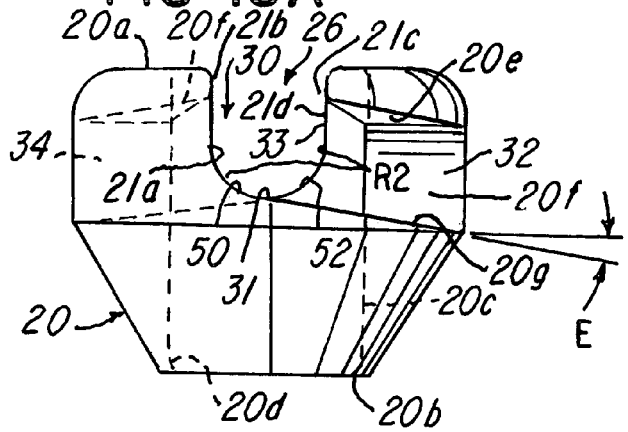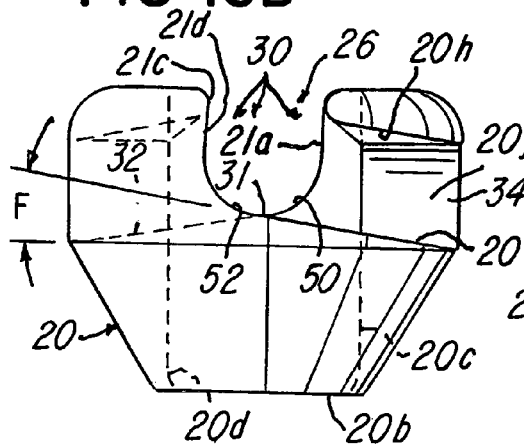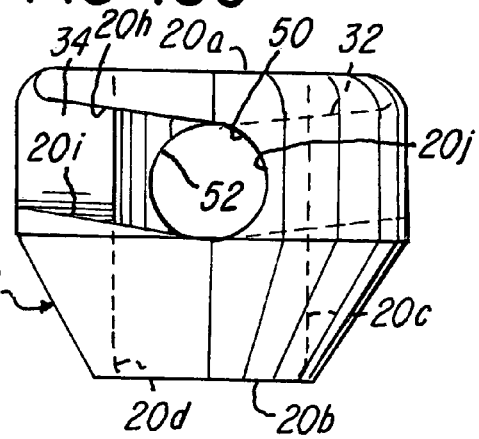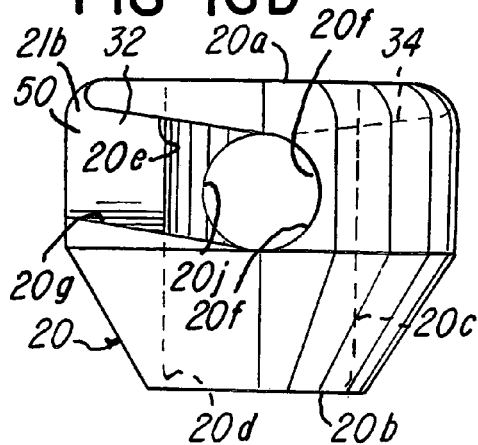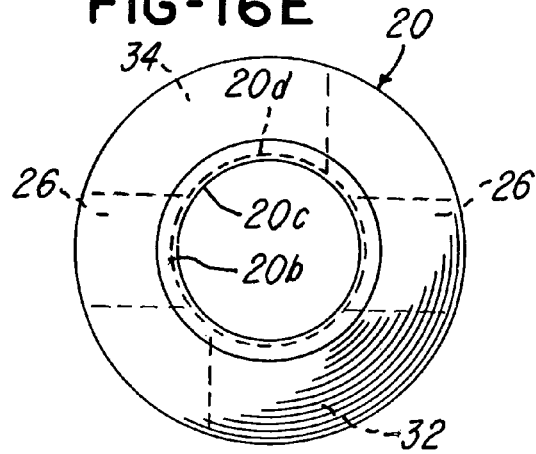

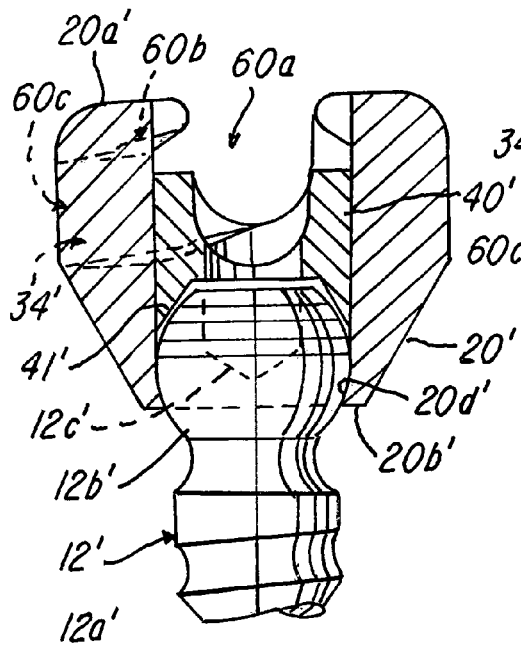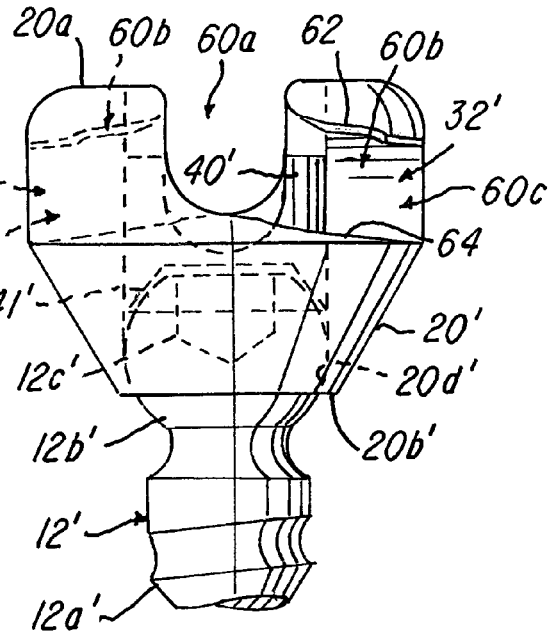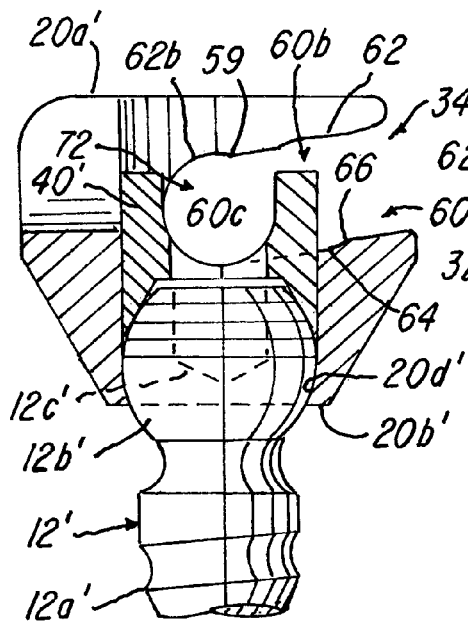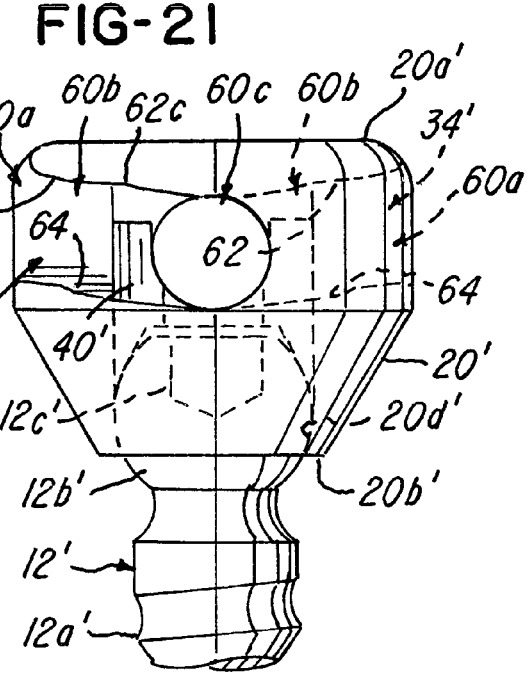

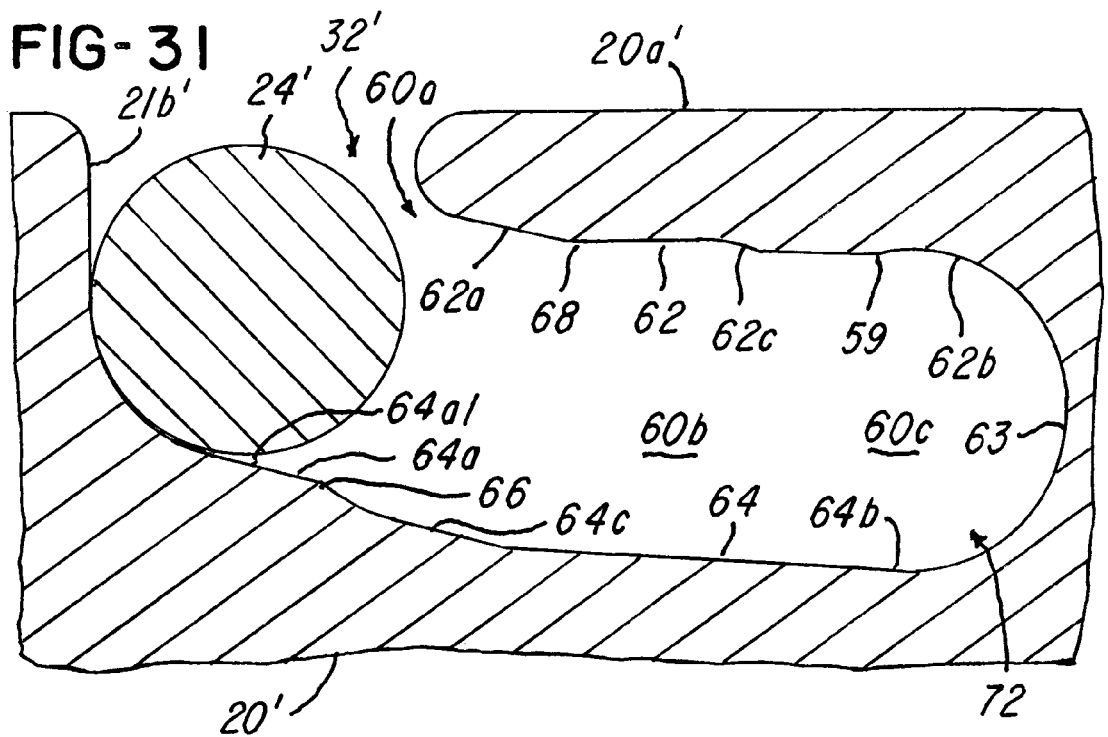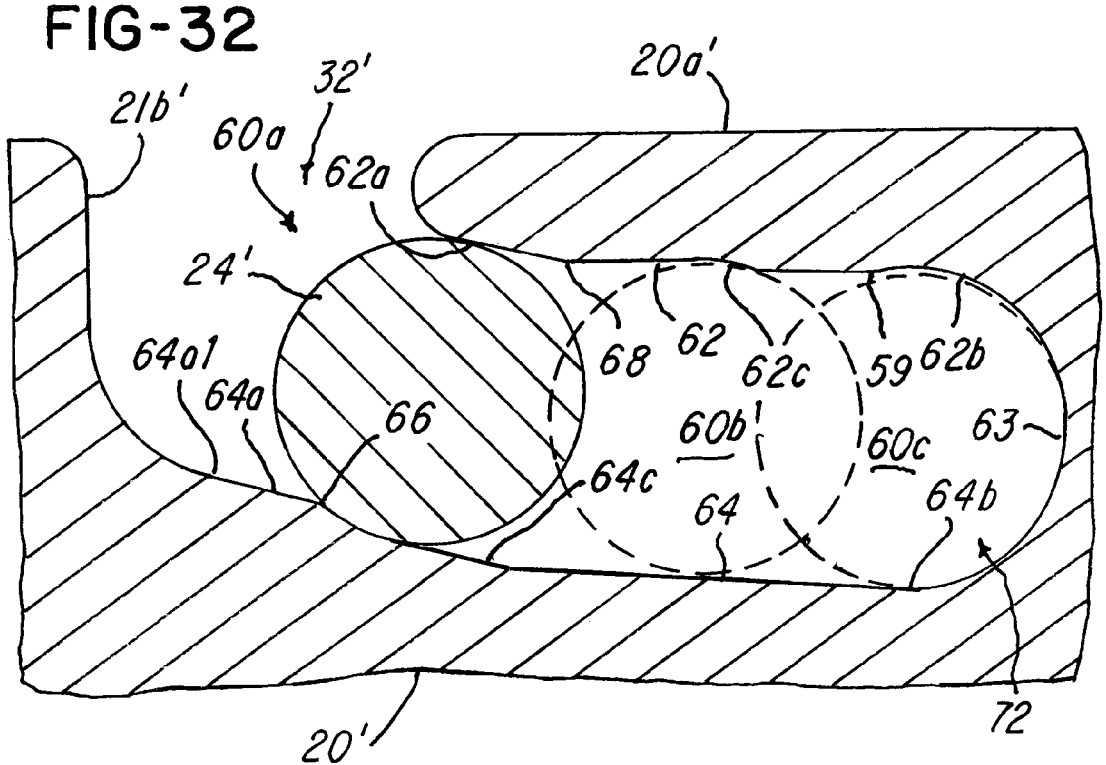

CAPLESS MULTIAXIAL SCREW AND SPINAL FIXATION ASSEMBLY AND METHOD

BACKGROUND OF THE INVENTION

This invention relates to a capless multiaxial screw and spinal fixation assembly and method, particularly useful for fixing and/or aligning vertebrae of the spine. The invention permits multiple angular orientations of an elongated member or rod with respect to a screw that is screwed into a vertebra.

Various methods of spinal immobilization have been known and used in the past. The preferred treatment for spinal stabilization is immobilization of the joint by surgical fusion or anthrodesis. This method has been known since development in 1911 by Hibbs and Albe. However, in many cases, in particular cases involving fusion across the lumbosacral articulation and where there are many levels involved, pseudorarthrosis is a problem. It was discovered that immediate immobilization was necessary in order to allow a bony union to form. Post operative external immobilization, such as the use of splints and casts, was a favored method of treatment, however, as surgical techniques have become more sophisticated, various methods of internal and external fixation have been developed.

Internal fixation refers to therapeutic methods of stabilization which are wholly internal to the patient and include commonly known devices such as bone plates and pins. External fixation, in contrast, involves at least some portion of stabilization device which is external to the patient's body. Internal fixation is now the favored method of immobilization because the patient is allowed greater freedom with the elimination of the external portion of the device and the possibility of infection, such as a pin tract infection is reduced.

There have been numerous systems and methods developed in the past for correcting and stabilizing and aligning the spine for facilitating, for example, fusion at various levels or areas of the spine, such as those devices are shown in U.S. Pat. Nos. 4,085,744; 4,269,178; 4,805,602; 5,466,237; 5,474,555; 5,891,145; and 6,869,433 B2. Bone screws with a polyaxial head are commonly used in spine surgery today. They are used chiefly in the lumbar spine and screwed into bone (pedicle) posteriorly. The head of the screw is attached to the shaft of the screw by means of a ball and socket. The top of the screw is machined into a ball, and the head contains a socket into which the ball fits. The screw head further contains a receiver for receiving a separate rod. The rod is fastened to the screw head receiver via a threaded cap. The rod is then fastened to screws placed in adjacent vertebrae thus providing stabilization. The polyaxial head allows the rod to be placed in a variety of angles with respect to the screw allowing conformance to local anatomy.

When the threaded cap is tightened upon the rod, a frictional pressure is transmitted from the threaded cap to the rod thence to the top of the ball, thus locking the ball-in-socket and preventing motion after tightening has occurred. This concept is demonstrated in U.S. Pat. Nos. 5,466,237 and 5,474,555, which illustrate this type of screw.

U.S. Pat. No. 5,466,237 to Bird et al. discloses a bone screw having a spherical projection on the top of the bone screw. An externally threaded receiver member supports the bone screw and spinal rod on top of the spherical projection. An outer nut is tightened onto the receiver member to press the spinal rod against the spherical projection to accommodate various angular orientations of the bone screw relative to the rod.

In another approach shown in U.S. Pat. No. 4,946,458 to Harms, a spherical headed bone screw supported within separate halves of a receiving member. The bottom of the halves are held together by a retaining ring. The top of the receiver halves are compressed about the bone screw by nuts threaded onto a threaded spinal rod.

In still another approach taken by Harms et al. in U.S. Pat. No. 5,207,678, a receiver member is flexibly connected about a partially spherical head of a bone screw. Conical nuts on opposite sides of the receiver member threaded onto a threaded rod passing through the receiver. As the conical nuts are threaded toward each other, the receiver member flexibly compresses around the head of the bone screw to clamp the bone screw in its variable angular position. One detriment of the systems in the two Harms et al. patents is that the spinal rod must be threaded in order to accept the compression nuts.

U.S. Pat. No. 6,869,433 discloses the use of a pedicle screw assembly that comprises a screw having a head with a convex portion and a receiver that receives the head. The receiver also receives an elongated member, such as a spinal fixation rod. The receiver has a concave portion which has a radius of curvature which is less than the radius of curvature of the convex portion of the head whereby to create an interference fit between the convex portion of the head and the concave portion of the receiver. The device also includes an internal nut and external nut that compresses the rod against a pressure disc which in turn compresses the head convex portion of the screw into the receiver concave portion and locks the angular position of the receiver with respect to the screw.

One of the problems with the prior art devices is the number of parts and components, especially those components that utilize a threaded cap screw to secure the rod to the anchoring screw, whether internal or external, to fix the rod relative to the screw. Problems with the threaded fastener, that is, threaded cap or set screw, are numerous and include risk of cap loosening, loss of cap intra-operatively, cross threading, thread failure, failure of the cap in driving instrument and limitations upon torque application.

What is needed, therefore, is a system and method that provide a lock or connection between the rod and screw without the use of external nuts, screws, caps or threads of the type shown in the prior art.

These and other objects and advantages of the invention will be apparent from the following description, the accompanying drawing and the appended claims.

SUMMARY OF THE INVENTION

The present invention improves the spinal fixation and the locking between an elongated member or rod and a screw.

One object of the invention is to provide a system and method that reduces or eliminates the need for external or internal caps or screws to lock the relative position of a rod to a screw.

Another object of the invention is to provide a simple bayonet-type connection that eliminates the fixation systems of the past and/or simplifies the spinal fixation procedure.

In one aspect, this invention discloses a capless multiaxial screw comprising a screw having a threaded portion and a screw head, a receiver having a bore for receiving the threaded portion and a receiving channel for receiving an elongated member, the channel further comprising a locking channel in communication with the channel, a compression member for situating in the bore, the compression member comprising a second receiving channel having a first end and a second end and further associated with a first end, and a receiving area associated with the second end for receiving and engaging the screw head, the elongated member cooperating with the compression member to lock the elongated member to the screw when the elongated member is received in the first and second receiving channels and the receiver is rotated from an unlocked position to a locked position.

In another aspect, this invention discloses a spinal fixation assembly comprising a receiver having a bore for receiving a screw having a screw head that is larger than a diameter of the bore, and a compression member dimensioned to be received in the bore and having a first end for receiving an elongated member and a second end for engaging the screw head, the receiver comprising a receiving channel for receiving the elongated member and a locking channel for locking the elongated member to the screw when the receiver is rotated from an unlocked to a locked position.

In yet another aspect, this invention relates to a spinal fixation assembly comprising a receiver having a bore for receiving a screw having a screw head that is larger than a diameter of the bore and a receiving channel for receiving an elongated member, and a compression member dimensioned to be received in the bore and having a first end for engaging the elongated member and a second end for engaging the screw head, the receiver comprising a rotary lock for locking the elongated member to the screw.

In still another aspect, this invention relates to a spinal fixation assembly comprising a receiver having a bore for receiving a screw having a screw head, and a compression member dimensioned to be received in the bore and having a first end for engagement with an elongated member and a second end for engagement with the screw head, the receiver comprising a locking channel and a receiving channel coupling the locking channels, the receiving channel receiving the elongated member and the locking channels cooperating to secure the elongated member to the screw when the receiver is rotated.

In another aspect, this invention discloses a spinal fixation assembly comprising a receiver having a bore for receiving a screw having a screw head, and a compression member dimensioned to be received in the bore and having a first end and a second end, the receiver comprising an integral rotary lock for locking the elongated member to the screw when the receiver is rotated.

In another aspect, this invention relates to a method for securing an elongated member to a spinal column, comprising the steps of screwing a screw into a spinal bone, the screw having a head that is received in a seat of a receiver having a bore through which threads of the screw may pass, situating the rod into the receiver, and rotating the receiver to fasten the rod onto the screw.

These and other objects and advantages of the invention will be apparent from the following description, the accompanying drawing and the appended claims.

BRIEF DESCRIPTION OF THE DRAWINGS

FIG. 1 is a fragmentary perspective view of a capless multiaxial screw and fixation assembly mounted on a spinal column having a plurality of vertebrae;

FIG. 2 is a perspective view of the system shown in FIG. 1;

FIG. 3 is an exploded fragmentary perspective view of the system shown in FIGS. 1 and 2;

FIG. 4 is a fragmentary perspective view illustrating a rod received in a receiving channel of a receiver;

FIG. 5 is a fragmentary plan view of the illustration shown in FIG. 4;

FIG. 6 is a fragmentary view similar to FIG. 4, but showing the receiver rotated approximately 30 degrees about its axis relative to the rod;

FIG. 7 is a fragmentary plan view similar to FIG. 5 and showing the receiver in the position illustrated in FIG. 6;

FIG. 8 is fragmentary perspective view showing the receiver in a fully locked position;

FIG. 9 is a plan view similar to FIGS. 5 and 7 showing the receiver in a fully locked position;

FIG. 10 is a view taken along the line 10-10 in FIG. 4;

FIG. 11 is a view illustrating the rod after it has been received in the channel of the receiver and supported above a bottom surface of a compression member;

FIG. 12 is a sectional view taken along the line 12-12 in FIG. 8;

FIG. 13 is a fragmentary view showing the rod in cross-section and in a fully locked position;

FIG. 16A-16E are various views of the receiver in accordance with one illustration of the invention;

FIG. 17 is a sectional view of a compression member in accordance with one illustration of the invention;

FIG. 18 is a fragmentary sectional view of another illustration of the invention, showing a channel having walls that are generally non-planar to define an intermediate area for loosely capturing the rod;

FIG. 19 is a side elevation view of the embodiment shown in FIG. 18;

FIG. 20 is a fragmentary sectional view that has been rotated relative to FIGS. 18 and 19;

FIG. 21 is an elevational view rotated relative to FIG. 19;

FIGS. 31-33 are fragmentary sectional views somewhat enlarged and diagrammatic to simply illustrate the intermediate capturing step of receiving area for loosely capturing the rod in the receiver.

DETAILED DESCRIPTION OF THE INVENTION

Figure 14:
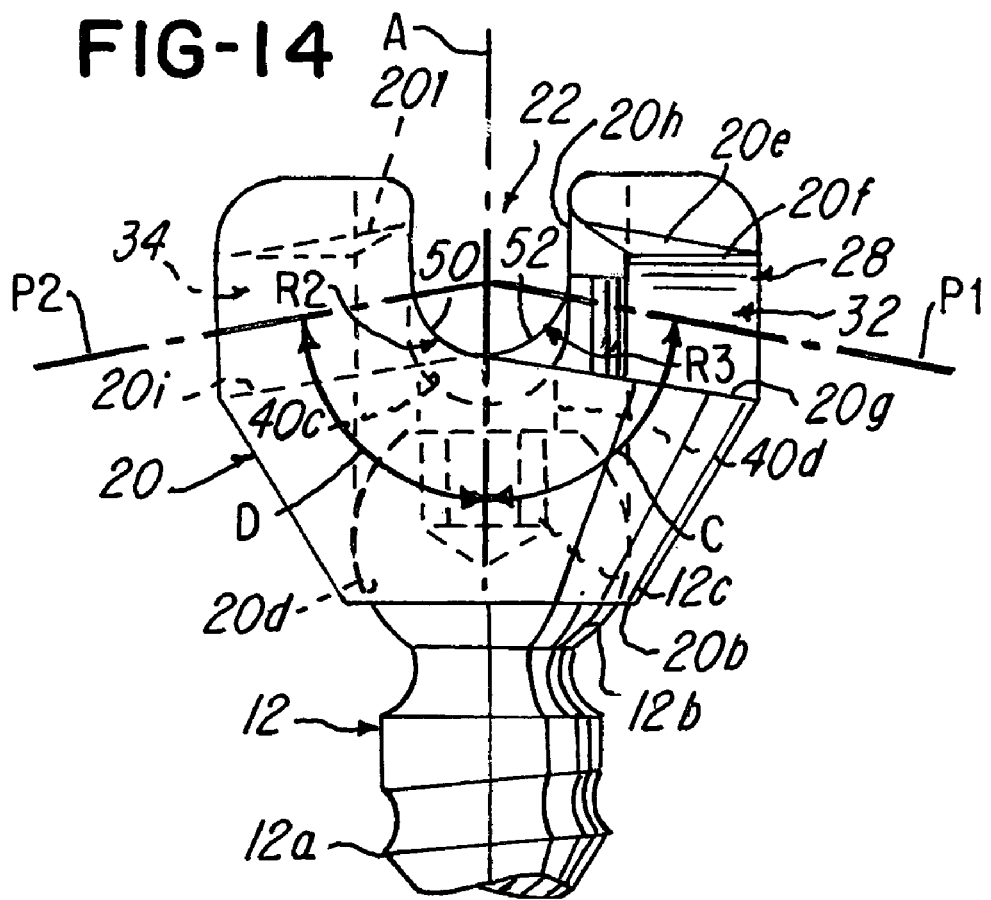
FIG. 14 is a fragmentary view illustrating various features of the locking channels.

Referring now to FIGS. 1-3, a capless multi-axial screw and spinal fixation assembly 10 and method are shown. The assembly 10 comprises a screw 12 having a threaded portion 12a and a head 12b that in the embodiment being described, has a rounded profile or curvature, as best illustrated in FIGS. 3 and 10-13. The screw head 12b comprises a hex female opening 12c for receiving a tool (not shown) for screwing the screw 12 into an aperture 14a of a spinal bone 14, such as a vertebra of a spine.

As illustrated in FIGS. 1 and 2, one feature of the invention is that it enables a user to fix a relative position of a plurality of vertebrae, such as vertebrae 14, 16 and 18 in FIG. 1, in a fixed and stabilized position.

Figure 15:
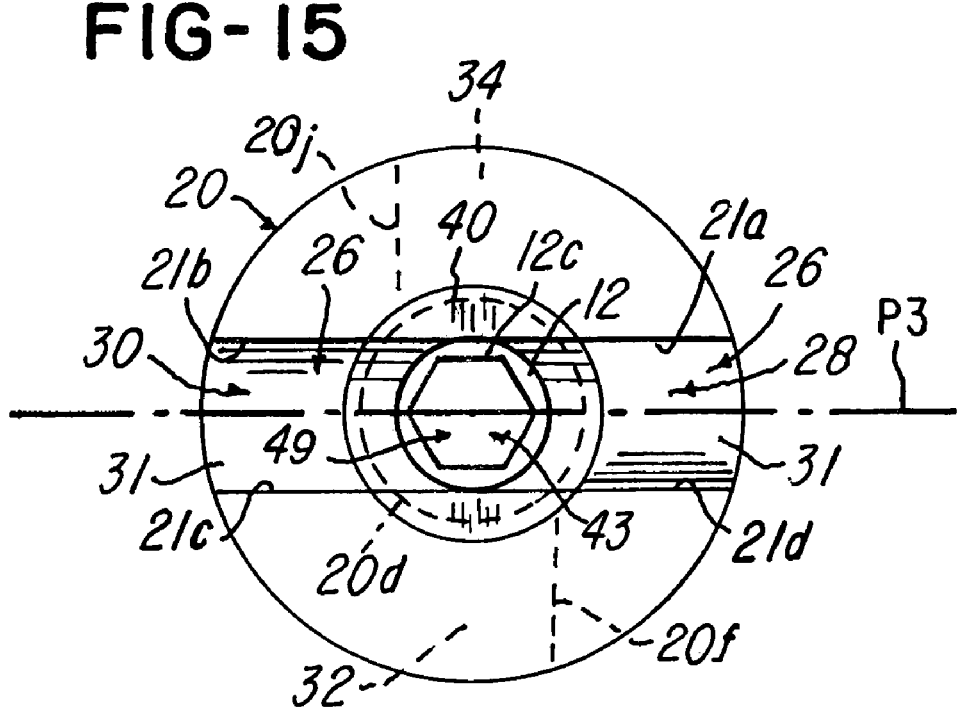
FIG. 15 is a plan view showing a compression member received in a bore of the receiver and illustrating the aperture through which a tool may be inserted to rotate the screw head before the rod is positioned in a channel of both the receiver and the compression member.

The assembly 10 comprises a retainer or receiver 20 having a generally cylindrical receiver wall 20c (FIG. 4) that defines an aperture or bore 22 that traverses or extends along a receiver axis A (FIG. 11) the entire length of the receiver 20, as best illustrated in FIGS. 4, 10, and 12. The receiver 20 comprises a first end 20a and a second end 20b, and although not shown, may comprise a chamfer 21 of about 45 degrees. It should be understood that the internal wall 20c defines a seat 20d toward the bottom of the receiver 20 (as viewed in FIGS. 10 and 15) that is arcuate or curved in cross section. The seat 20d has a radius or curved surface R1 (FIG. 10). Note that a diameter or distance D1 (FIG. 10) of bore 22 at the end 20b of the receiver or retainer 20 is slightly smaller than both a diameter or distance D2 (FIGS. 7 and 10) of the bore 22 at end 20a and a diameter D3 (FIG. 12) of the rounded screw head 12b so that it defines the receiver seat 20d (FIGS. 10 and 15) for receiving or capturing the screw head 12b. In this regard, the screw head 12b has an end 12b1 that is configured and dimensioned to be received or captured in the seat 20d and that can be rotated or screwed while in the bore 22 (FIGS. 10 and 15). The end 12b2 has a curved or arcuate shape that generally complements the shape of the seat 20d to permit polyaxial and relative movement between the receiver 20 and screw 12.

As shown in FIGS. 3 and 11-13, the bore 22 receives the threaded portion 12a of the screw 12 until the head 12b is received in the seat 20d (as illustrated in FIGS. 10-13). It should be understood that the seat 20d cooperates with the end 12b1 of head 12b and permits the retainer or receiver 20 to move polyaxially about a center of head 12b so that position of the receiver 20 may be altered relative to the head 12b of screw 12. This allows a user, such as a surgeon or physician, to change the polyaxial position of the receiver 20 relative to the screw 12 in order to adjust an angular position of an elongated member or rod 24 relative to, for example, the vertebrae 14, 16 and 18 illustrated in FIG. 1. The rod 24 may be any suitable shape in cross section, such as circular, hexagonal, octagonal, polygonal or the like.

Note that the receiver 20 comprises a receiving channel or slot 26 (FIG. 15) defined by wall surfaces 21a, 21b, 21c and 21d (FIG. 4). The receiver 20 further comprises a lock, locking means, locking channel, or rotary lock 28 (FIGS. 11 and 12) which is integral with the receiver 20. In the embodiment being described, the receiver 20 is manufactured of titanium and is machined to provide the receiving channel 26, lock 28 and the bore 22 using conventional machining techniques. Other potential materials include biocompatible load bearing material, such as metals, metal alloys, carbon fibers, composites, plastics or hybrid materials.

In one embodiment, the lock 28 cooperates and is in communication with the receiving channel 26 to provide a continuous channel 30 for receiving the elongated member or rod 24. The lock 28 cooperates with the receiving channel 26 and urges rod 24 toward the screw head 12b and vertebra, such as one of the vertebra 14-18 in FIG. 1, when the receiver 20 is rotated in a clockwise direction (as viewed in FIG. 3). The continuous channel 30 comprises a first channel 32, the channel 26, and the second channel 34. The lock 28 and continuous channel 30 provides a bayonet-type connection for coupling or fixing the receiver 20, the rod 24 and screw 12 together in the manner described herein.

Note that the lock 28 comprises the first channel 32 and a second channel 34 (FIGS. 12 and 13) that extend or spiral, as illustrated in FIGS. 16A-16E, about the receiver axis A (FIG. 11) of receiver 20. The first and second channels 32 and 34 generally spiral or revolve from the first end 20a of receiver 20 toward the second end 20b, as shown in FIGS. 10-13 and 16A-16D. Thus, in the embodiment being described, the first and second channels 32 and 34 are non-linear and spiral or revolve in a general helix about the axis A of the receiver 20. In the illustration, the channels 32 and 34 spiral or revolve in the same direction about the axis A, as shown in FIGS. 16A-16D. Note that the channels 32 and 34 are in communication with both the receiver bore 22 and receiving channel 26 of receiver 20. During operation, the channels 32 (FIG. 11) and 34 (FIG. 12) receive the rod 24 after it has been received in channel 26 and urge or force the rod 24 toward the screw head 12b and vertebra, such as vertebra 14 in FIG. 1, when the receiver 20 is rotated in a clockwise direction in the illustration being described.

As illustrated in FIGS. 11 and 16A, the first channel 32 is defined by a first surface or wall 20e, a generally opposing second surface or wall 20g, and a third surface or wall 20f that joins the walls 20e and 20g in the receiver 20. A fourth surface or wall 20h, a generally opposing fifth surface or wall 20i, and a sixth surface or wall 20j that joins walls 20h and 20i cooperate to define the second channel 34 (FIGS. 12 and 16D). Note that the walls 20e and 20g are generally parallel and walls 20h and 20i are generally parallel. In the illustration being described, the walls 20e and 20g and 20h and 20i are generally planar and have generally constant distance D4 (FIG. 13) and D5 (FIGS. 11 and 12) therebetween. However, in the illustration described later herein relative to FIGS. 18-32, the opposing walls 20e, 20g, 20h and 20i may be non-planar so that the distance or dimensions D9 and D10 vary along the length of the channels 32 and 34.

The channels 32 and 34 generally lay in planes P1 and P2 that are at the angles C (FIG. 14) and D, respectively, relative to the axis A of the receiver 20. As described later herein, the walls 20e and 20h engage and cam against the rod 24 and force or urge it downward (as viewed in FIGS. 10-15) in response to the rotary movement of the receiver 20. In another embodiment described later herein, the walls 20e and 20g and walls 20h and 20i may comprise a curved or arcuate area and may cooperate to define an intermediate rod capturing area, as described below relative to FIGS. 18-34.

As illustrated in FIGS. 4 and 11, note that the channel 32 is defined by the walls 20e, 20f, 20g and generally curved or arcuate wall portion 50 that couples wall 20g to surface 21b (FIGS. 4 and 16A) of channel 26. The generally curved arcuate wall portion 50 also generally defines an intersection or transition from the receiving channel 26 to the first locking channel 32 of lock 28. The channel 34 is defined by 20h, 20i and 20j and a third generally curved or arcuate wall 52 that joins the wall 20i to wall surface 21d (FIGS. 4 and 16C). The wall 52 provides an intersection or transition between channel 26 and the second locking channel 34. Notice that the wall portions 20f (FIG. 11) and 20j (FIG. 12) also each have a radius of curvature that generally complements the radius of curvature or circumference of the rod 24 so that when the rod 24 is moved from the unlocked position (illustrated in FIGS. 4, 5, 10 and 11) to a locked position (illustrated in FIGS. 8, 9, 12 and 13), the rod 24 is received and positioned against the wall portions 20f and 20j as shown.

The assembly 10 may further comprise a compression member 40 (FIGS. 3 and 17). The compression member 40 comprises a wall 40a that defines a second generally U-shaped receiving channel 42. The compression member 40 also comprises a frusto-conical seat or concave area 41 (FIGS. 10 and 17), defined by a tapered wall or surface 40b, that engages the rounded shape of the end 12b1 (FIG. 3) of screw head 12b. Although not shown, the assembly 10 could be provided without the compression member 40, so that the rod 24 would engage the screw head 12b directly, for example, when the receiver 20 is rotated as described later herein.

The compression member 40 comprises a length D6 (FIGS. 3 and 17) and a diameter D7 (FIG. 17) dimensioned to be received in the bore 22 as shown. The channel 42 defined by wall 40a comprises a bottom surface 40c. The channel 42 is generally U-shaped in cross section and has a width or dimension D8 (FIGS. 3, 7 and 17) and surface 40c comprises a radius of curvature R5 (FIG. 17) that generally complements or is slightly larger than the circumference D9 (FIG. 3) of the rod 24.

During operation, the compression member 40 is urged downward (as shown in FIGS. 10-13) in response to the rotary movement of the receiver 20. The rod 24 engages the bottom surface 40c (FIGS. 12 and 17) of channel 42 of compression member 40. This in turn causes surface 40b to engage and apply a compressive force against the end 12b1 of screw head 12b as the rod 24 is driven in the downward direction (as viewed in FIGS. 10-13) and into the second channel 42. This movement forces and compresses the seat 20d against the end 12b2 of screw head 12b of the receiver 20, thereby locking the screw head 12b to the rod 24 and fixing the relationship of the receiver 20 relative to the screw head 12b.

Note that the compression member 40 (FIG. 17) also comprises a bore or aperture 43 defined by wall 40d. The bore 43 has a dimension or diameter D10 (FIG. 17). A surgeon or physician may insert a tool, such as a hex head screwdriver (not shown), through channel 26, through bore 22 of receiver 20 and through the bore 43 and into the hex female opening 12c (FIG. 15), for example, to tighten or loosen the screw 12. Thus, it should be understood, as illustrated in FIG. 15, that the hex female opening 12c of screw head 12b is accessible after the screw 12 is inserted through the bone 22 and compression member 40 is situated in the bore 22.

Referring back to FIGS. 10-16E, the receiving channel 26 (FIG. 11) of receiver 20 extends from an end 20a of receiver 20 in an axial direction and lies in a plane P3 (FIG. 15) that is generally planar and extends downward along the axis A (as viewed in FIG. 14). In contrast, the lock 28 defined by the locking channels 32 and 34 revolve, spiral or extend laterally or radially at distances that are generally constant relative to axis A and that vary, such as increase, relative to end 20a of receiver 20. As mentioned earlier, each of the channels 32 and 34 spiral in a general helix downward from the receiving channel 26 and about the axis A of the receiver 20 as shown in FIGS. 10-13 and 16A-16D. Note that the channels 32 and 34 lay in the planes P1 and P2 (FIG. 14), respectively, that intersect axis A at the predetermined angles indicated by double arrows C and D. The predetermined angles C and D are acute angles in the embodiment being described.

As shown in FIGS. 16A and 16B, the channel 32 is inclined relative to a radial line of receiver 20 at a third angle (indicated by double arrow E in FIG. 16A) relative to end 20a. Channel 34 is also inclined relative to a radial line at a fourth angle F (FIG. 16B). Although not shown, it is contemplated that other designs, configurations or arrangements of channels 32 and 34 and the lock 28 may be provided, such as channels (not shown) that extend about axis A, but that do not spiral and/or that are not at the inclined angles E and F, such as channels that extend at distances that are generally constant relative to end 20a.

An operation or method regarding this illustration will now be described. As illustrated in FIGS. 3-9 and 15, the screw 12, together with receiver 20 are screwed into vertebra 14 during which a physician or surgeon screws the threaded portion of screw 12 in the aperture 14a of the vertebra 14 using a tool (not shown), such as a hex wrench or screwdriver (not shown), that is inserted through channel 26, bore 22 and bore 43. In one embodiment, the receiver 20, screw 12 and compression member 40 may be provided in a pre-assembled unit prior to surgery, so no assembly is required by the physician. The screw 12 is screwed substantially all the way into vertebrae 14, but is left with space between the receiver 20 and vertebrae 14 so that an angular or polyaxial position of the receiver 20 may be adjusted or changed during the operation.

The channel 26 of receiver 20 and channel 42 of compression member 40 are provided or arranged in a common plane P3, as shown in FIGS. 4, 5 and 15. The surgeon then places the rod 24 into the channels 26 and 42 and adjusts the multi-axial or polyaxial position of the receiver 20 relative to the rod 24. As mentioned earlier, the channel 26 and bores 22 (FIG. 10) and 43 (FIG. 17) provide a continuous opening or area 49 through which the physician or surgeon may insert a tool, such as a hex tool, to turn, rotate and/or tighten or loosen the screw 12 in the desired direction prior to placing the rod 24 into channel 26. At this point, the rod 24 remains in an unlocked position.

Note that the rod 24 is supported by and between the arcuate or rounded wall portions 50 and 52, which causes the rod 24 to be situated above the bottom surface 40c of the channel 42 of compression member 40, as illustrated in FIGS. 10 and 11. Note that the arcuate or curved wall portions 50 and 52 each comprise a radius of curvatures R2 (FIGS. 11, 14 and 16a) and R3 (FIGS. 13 and 14), respectively, that generally complements or is larger than a radius of curvature or circumference of the rod 24, as illustrated in FIGS. 11 and 13.

The camming or bayonet type action of the rotary lock 28 on receiver 20 forces the rod 24 in an axial direction parallel with axis A of receiver 20 when the receiver 20 is turned or rotated with a tool, such as a screwdriver (not shown), placed in channel 26, as illustrated in FIGS. 6 and 7. This rotary movement or action forces the rod 24 downward (as viewed in FIG. 10) and into the channels 32 and 34. As the receiver 20 is rotated further, as shown in FIGS. 8 and 9, the walls 20e and 20g (FIG. 11) of channel 32 and walls 20h and 20i (FIG. 12) of channel 34 act upon, force or urge the rod 24 downward (as viewed in FIGS. 10-13) and into the second channel 42 of compression member 40 until it engages the surface 40c of compression member 40. As the receiver 20 is rotated further, the rod 24 urges the compression member 40 toward the screw head 12b and forces wall 40b of the compression member 40 against the screw head 12b of screw 12 with a compressive force which causes the screw head 12b to become fastened or locked to the rod 24, thereby fixing the receiver 20 and rod 24 to the screw 12.

It should be appreciated that when the rod 24 is in the locked position shown in FIGS. 8, 9, 12 and 13, the rod 24 engages surfaces 20e, 20f, and 20g of channel 32 and surfaces 20h, 20i and 20j of channel 34 and surface 40c of second channel 42. The wall 40d of compression member 40 engages screw head 12b. These surfaces cooperate to retain rod 24 in the locked position. The surfaces 20f and 20j comprise a radius of curvature R4 of about φ.100-φ.130 inch. A raised detent portion or bump 59 (which is only shown in FIG. 13 for ease of illustration) may be provided in each channel 32 and 34, as shown in FIG. 13 relative to channel 32. The detent 59 is provided to facilitate retaining the rod 24 in the locked position.

Thus, as illustrated in FIGS. 1, 2 and 4-9, a surgeon may use one or a plurality of spinal fixation assemblies 10 during a spinal fixation procedure. For example, the surgeon may use a plurality receivers 20 and screws 12 with one rod 24, as illustrated in FIGS. 1 and 2. In the illustration, the surgeon screws the screws 12 into a plurality of vertebrae, such as vertebrae 14, 16 and 18 illustrated in FIG. 1, and generally aligns the channels 26 of receivers 20. The surgeon then inserts the tool, such as a hex tool (not shown), through bores 22 and 43 and into hex female opening 12*c* in screw head 12*b* and screws the screw 12 until the bottom 20*b* of the receiver 20 engages or is proximately located against its respective vertebra.

If the compression member 40 is being used, compression member 40 is located in each bore 22 of each receiver 20 and generally aligns the channels 42 and 26, as illustrated in FIGS. 4, 10 and 15. It should be understood that when the spinal fixation assembly 10 is in the unlocked position, the channels 26 and 42 are generally parallel or lie in the common plane P3 as shown in FIG. 15. The rod 24 is then placed in channel 26, whereupon it becomes supported by walls 50 and 52 (FIG. 4) and by wall portions 50 and 52 (FIGS. 4 and 11). This causes rod 24 to be supported slightly above the bottom 40*c* of channel 42 of receiver 20, as mentioned earlier and as illustrated in FIGS. 10 and 11.

At this point in the procedure, the surgeon aligns the rod 24 in the receiver 20 to the desired position relative to the spine, vertebrae and other receivers 20 that are being used. He positions the rod 24 and polyaxial or angular position of each receiver(s) 20 relative thereto. It should be understood that the screws and position of the vertebrae, such as vertebrae 14-18, relative to each other may also be adjusted. Once the bones 14-18 are adjusted and angular or polyaxial position of each receiver 20 is adjusted, the surgeon locks each receiver 20 to rod 24 by rotating or turning the receiver 20 with a tool, such as a screwdriver (not shown), placed in slot 26. This causes the receivers 20 to become fixed or locked onto their respective screws 12 and the spinal bones 14-18 (FIG. 1) to become aligned and fixed into the desired position.

It should be understood that before the rod 24 is placed in the receiving channel 26 and the receiver 20 is rotated, the surgeon may tighten one or more screws 12 to a tighter or fixed seated position by situating the tool, such as a hex wrench (not shown), through the aperture 43 (FIG. 15) defined by the wall 40*d* of the compression member 40 and into the hexagonal female slot 12*c* in the screw head 12*b*. After the screw 12 is tightened to the desired tightness or torque, the surgeon places the rod 24 into the channels 26 and 42 (FIGS. 4, 5, 10 and 11) of the one or more of the receivers 20 being used.

As mentioned, the surgeon rotates the receiver 20 about its axis, as illustrated in FIGS. 3, 6 and 7 using a tool, such as a screwdriver (not shown), in the clockwise direction, as illustrated in FIGS. 6 and 7. During this rotation of receiver 20, the compression member 40 and rod 24 do not rotate. As alluded to earlier, walls 20*e* and 20*g* (FIG. 11) and walls 20*h* and 20*i* (FIG. 12) urge the rod 24 toward the bottom of channels 32 and 34 and urge the rod 24 to move downward (as viewed in FIGS. 10 and 12) toward the surface 40*c* or bottom of the channel 42 where it engages the surface 40*c*, as illustrated in FIGS. 4-9 and 10-13. The rod 24 is also supported by and compresses against the surface 40*c* of compression member 40. The wall 40*d* is caused to engage the screw head 12*b*.

Thus, when it is desired to lock the receiver 20 and the screw 12 to the rod 24, the surgeon rotates the receiver 20 in the clockwise direction, as illustrated in FIGS. 6 and 7, using the conventional tool, such as a regular screwdriver. The receiver 20 is rotated until it is moved from the unlocked to the locked position, as illustrated in FIGS. 8, 9, 12 and 13. Note that in the locked position, the rod 24 is received and engages the walls 20*f* and 20*j* associated with the ends of channels 32 and 34, respectively.

Thus, it should be understood that when receiver 20 is rotated, the walls 20*e* and 20*h* provide the camming force necessary to cam and urge the rod 24 against the compression member 40. This, in turn, causes the surface or wall 40*b* of compression member 40 to compress and lock against the end portion 12*b*2 (FIG. 3) of screw head 12*b*. The wall 40*b* of compression member 40 cooperates with the curved seat 20*d* defined by wall 40*b* (FIG. 10) and traps or locks the screw head 12*b* to the rod 24.

As illustrated in FIGS. 8, 9, 12 and 13, notice that the channel 26 lies in an imaginary plane that is generally perpendicular to the imaginary plane in which the channel 42 and an axis of rod 24 when the receiver 20 is in the locked position.

It should be appreciated from the foregoing that the receiving channel 26 is in communication with the channels 32 and 34 of lock 28 and that the lock 28 cooperates with the rod 24 to not only lock the rod 24 to the screw 12, but also to fix a position of the vertebrae 14, 16 and 18.

When it is desired to unlock the rod 24 from the screw 12, the surgeon simply rotates the receiver 20 in a counterclockwise direction in the illustration and reverses the procedure.

Referring now to FIGS. 18-34, another illustrative embodiment is shown. Those parts that are the same as the parts relative to FIGS. 1-17 have been labeled with the same part number, except that the part numbers in the embodiment described in FIGS. 18-34 have a prime mark ("'") associated therewith. The FIGS. 31-34 are diagrammatic enlarged sectional views for ease of illustration.

Note in the embodiment in FIGS. 18-34, the receiver 20' comprises channels 32' and 34' that each have a cross-sectional dimension that varies over the length of the channels 32' and 34' to provide an introducing area 60*a* where the rod 24' is loosely captured in the channels 32' and 34'. The channels 32' and 34' each have an introducing area 60*a*, an intermediate holding or receiving area 60*b* and a locking area 60*c*. For ease of illustration and description, the receiving area 60*b* will be described relative to channel 32'; however, it should be understood that the channel 34' in the second illustration comprises substantially the same configuration.

Figure 23:
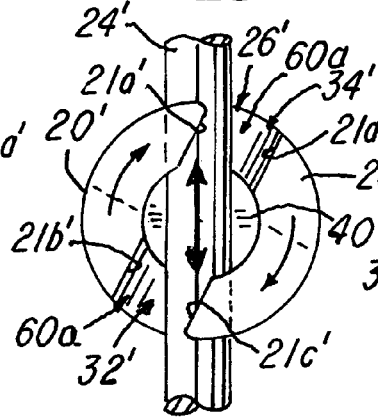
Figure 24:
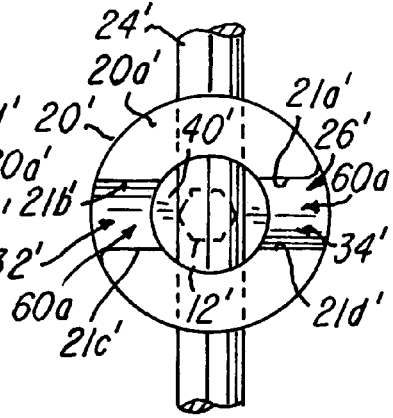
Figure 26:
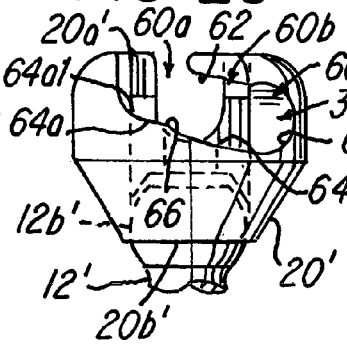
Figure 27:
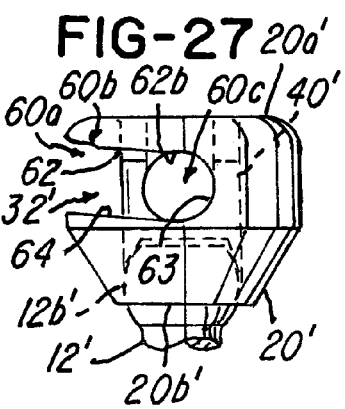
Figure 29:
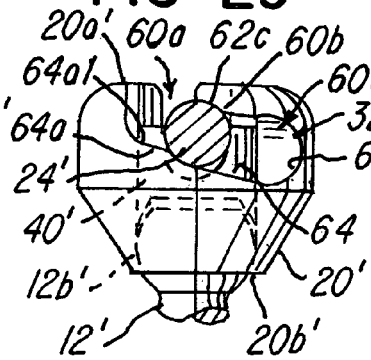
Figure 30:
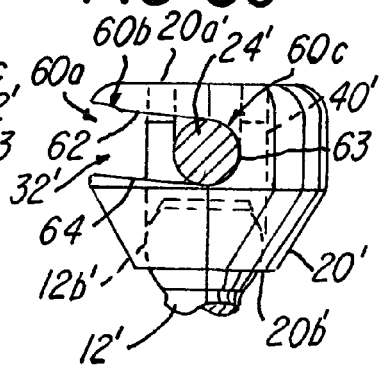
Figure 33:
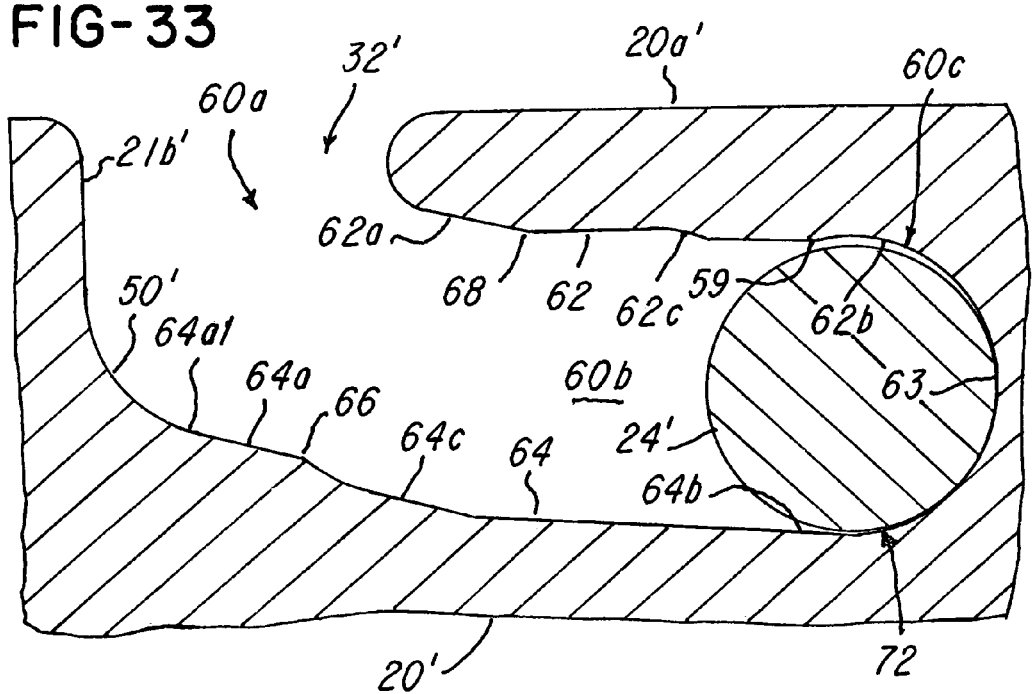

It should be appreciated that the intermediate area 60*b* in the channels 32' and 34' enable an intermediate step between initial rod 24' insertion and final rod 24' locking. In other words, this is a rod 24' capturing step during which the rod 24' is loosely captured in the receiver 20', but it is not rigidly locked into place against screw 12' yet. This allows the surgeon greater ease and flexibility when he adjusts the screws 12' position with respect to the rod 24' while the rod 24' is in place. For example, the surgeon may move the screws 12' closer together (compression) or In the illustration being described, the intermediate capturing step is accomplished by rotating the receiver 20' partially, such as approximately 30 degrees in the illustration as shown in FIGS. 23, 26 and 29, which forces the rod 24' from the introducing area 60*a* into the intermediate area 60*b*.

Figure 34:
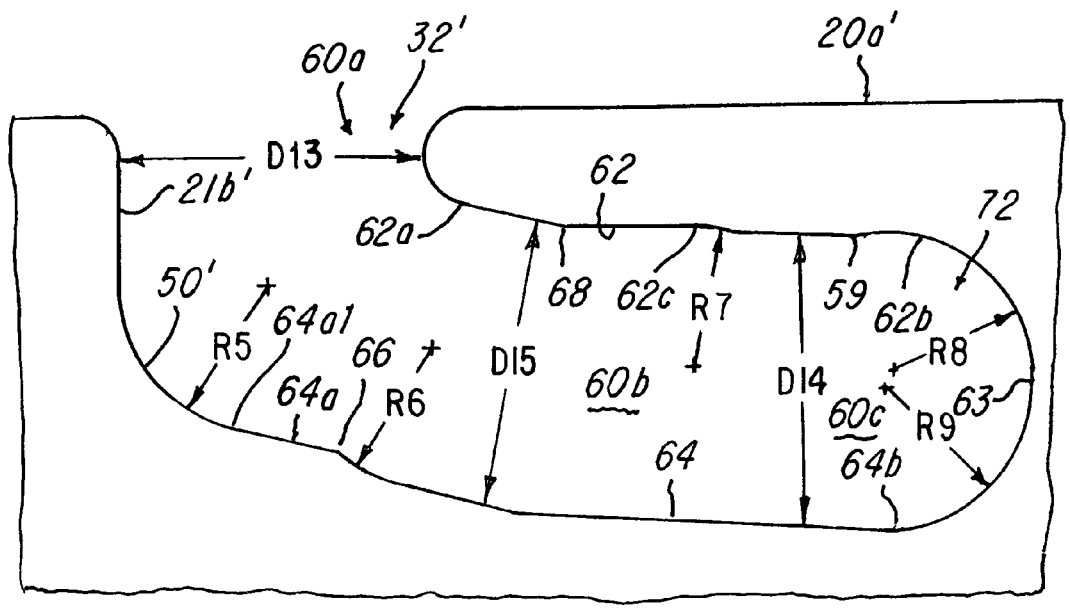
FIG. 34 is a diagrammatic view which is presented for purposes of illustrating various dimensions of the channels in the receiver or the second illustrative embodiment.

The introduction area comprises an associated dimension D13 (FIG. 34) and the locking area 60*c* has an associated dimension D14 (FIG. 34). The intermediate area 60*b* has an associated intermediate dimension D15 (FIG. 34) between the wall 62 and wall 64 that is slightly larger than the diameter of the rod 24' and the dimensions D13 and D14 associated with the introduction area 60*a* and locking area 60*c*, respectively. It is dimensioned to accommodate the rod 24' and to capture the rod 24' loosely so that the rod 24' can easily slide between the walls 62 and 64 and is not locked. This facilitates the surgeon adjusting a position of the screws 12' in vertebrae, such as vertebrae 14'-18', relative to a position of the rod 24. Once the screws 12' are adjusted to the desired position, the physician or surgeon may then lock the receiver 20' onto the screw 12' by inserting a tool, such as a screwdriver (not shown), into the slot 26' and rotate the receiver 20' in the clockwise direction as illustrated in FIGS. 22-30.

In the illustration shown in FIGS. 31-34, the channel 32' is defined by a wall 62, a generally opposing second wall 64 and a joining wall 63 that joins walls 62 and 64 as shown. Note that unlike the embodiment described relative to FIGS. 1-17, the channel wall 62 has a first wall portion 62a, a second wall portion 62b and an intermediate wall portion 62c that couples the wall portions 62a and 62b as shown. The opposing channel wall 64 comprises the first wall portion 64a, a second wall portion 64b and an intermediate wall portion 64c that couples the first and second wall portions 64a and 64b as shown. In this regard, note that an intersection 66 is defined between the wall portions 64a and 64c. A second intersection 68 is defined between the wall portion 62b and 62c as shown. The intersections 66 and 68 generally define an entrance to the intermediate area 60. The intermediate wall portions 62c and 64c cooperate to define the intermediate area 60b which receives the rod 24' and loosely captures the rod 24' in the receiver 20'.

Figure 22:
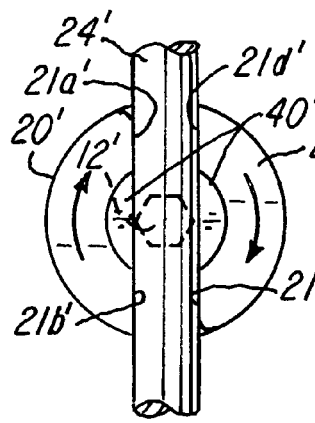
FIGS. 22-24 are plan views illustrating rotational movement of the receiver relative to the rod.
Figure 25:
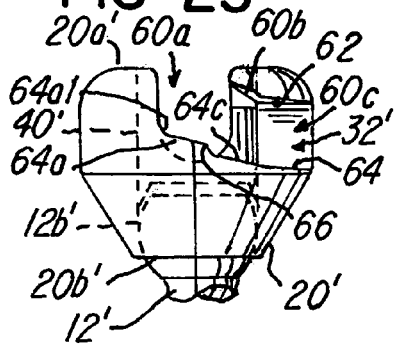
FIGS. 25-27 are side elevation views that generally correspond to FIGS. 22-24, respectively, illustrating the receiver in various positions, but with the rod removed for ease of illustration and understanding.
Figure 28:
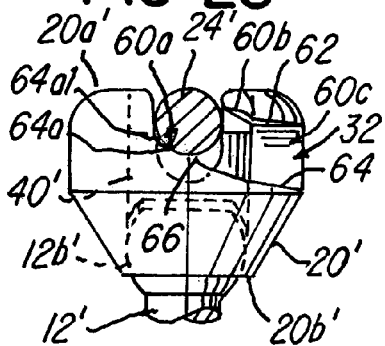
FIGS. 28-30 are views similar to FIGS. 25-27, respectively, illustrating the receiver in various rotational positions relative to the rod as the rod is moved from a receiving position to a locked position.

The channels 32' and 34' are configured such that they comprise or define the introduction area 60a for receiving the rod 24' in the receiver 20', as illustrated in FIGS. 22, 25 and 28. The first wall portion 64a provides a ramp 64a1 for directing the rod 24' into the intermediate area 60b when the receiver 20' is rotated about 20-40 degrees as shown in FIGS. 23, 26 and 29. As shown in the illustration, the walls 62 and 64 are not generally planar and have areas, such as intermediate wall portions 62c and 64c that are curved or recessed to facilitate defining the intermediate area 60b.

During a surgical procedure, the surgeon may make the desired adjustments of the rod 24' relative to the screws 12' and vertebrae 14'-18' while the rod 24' is loosely captured in the intermediate area 60b. The surgeon then uses the tool, such as a screwdriver (not shown), to rotate the receiver 20' to the locked position shown in FIGS. 24, 27 and 29. Similar to the embodiment described earlier herein relative to FIGS. 1-17, the receiver 20' urges or forces the rod 24' from the intermediate area 60b to the locking area 60c. The rod 24' becomes situated in the locking area 60c, whereupon the rod 24' becomes locked therein. Note that the distance or dimension D12 (FIG. 8) between the second wall portions 64b and 62b is substantially the same or may be smaller than the diameter of the rod 24'. As the receiver 20' is rotated in the clockwise direction in the illustration being described, the wall 62 slightly deflects upward (as viewed in FIG. 31, for example) to permit the rod 24 to be captured and locked in the locking area 60c. Note that a wall portions 62, 63 and 64 comprises various radii of curvature R5-R9 having the illustrative dimensions or ranges of dimensions set forth in the Table I below. For example, the radius of curvature R8 generally corresponds to the cross sectional circumference of the rod 24' so that the rod 24' becomes captured in the locking area 60c. As in the prior illustration, the detent 59 (FIG. 33) may be provided in channels 60 and 62 to further facilitate retaining the rod 24' in the locking area 60c.

Advantageously, this system and method facilitates providing a locking receiver 20 that reduces or eliminates the need for threading, internally or externally.

Advantageously, the immediate areas 60b of channels 32' and 34' of the second embodiment are dimensioned and configured to facilitate locking the rod 24' onto the screws 12' while permitting ease of adjustment between the receiver 20' and the rod 24' when the rod 24' and receiver 20' are situated in the intermediate area 60b', as illustrated in FIGS. 23, 26 and 29.

In the embodiments being described, the rod 24, screw 12, receiver 20 and compression member 40 are all made of titanium alloy. Other materials may be used such as metals, metal alloys, carbon fibers, composites, plastics or hybrid materials. Various illustrative dimensions or possible ranges of dimensions are listed in the following Table I:

| Part Number/Label | Illustrative/Approximate Dimensions/Ranges |
|---|---|
| D1 (FIG. 10) | φ.302 inch |
| D2 (FIG. 10) | φ.350 inch |
| D3 (FIG. 12) | φ.890 inch |
| D4 (FIG. 13) | φ.590 inch |
| D5 (FIG. 11) | φ.230 inch |
| D6 (FIG. 3) | φ.400 inch |
| D7 (FIG. 17) | φ.348 inch |
| D8 (FIG. 3) | φ.240 inch |
| D9 (FIGS. 3) | φ.218 inch |
| D10 (FIG. 17) | φ.200 inch |
| D11 (FIG. 3) | 10 mm-60 mm |
| D12 (FIG. 8) | 2 mm-10 mm |
| D13 (FIG. 34) | φ.225 inch |
| D14 (FIG. 34) | φ.220 inch |
| D15 (FIG. 34) | φ.210 inch |
| R1 (FIG. 10) | φ.115 inch |
| R2 (FIG. 14) | φ.340 inch |
| R3 (FIG. 14) | φ.340 inch |
| R4 (FIG. 12) | φ.100-φ.130 inch |
| R5 (FIG. 34) | φ.115 inch |
| R6 (FIG. 34) | φ.100 inch |
| R7 (FIG. 34) | φ.115 inch-φ.130 inch |
| R8 (FIG. 34) | φ.110 inch |
| R9 (FIG. 34) | φ.100 inch-φ.130 inch |

For example, the screw 12 may have a length D11 (FIG. 3) ranging from 10 mm-60 mm, and the receiver 20 may have a diameter D12 (FIG. 8) ranging between 2 mm-10 mm. The compression member 40 may define the channel 42 having the width D8 ranging between 2 mm-12 mm. The channels 32 and 34 may comprise dimensions D5, D6 (FIGS. 3 and 17) ranging between 2 mm-10 mm. It should be understood, however, the other shapes and dimensions may be used without departing from the true spirit and scope of the invention.

Advantageously, this system and method provide a capless multiaxial screw which eliminates the need for caps or screws or threads of the type used in the prior art. This system and method combine a very simplified yet effective means for locking an elongated member or rod 24 to a screw 12 and spinal bone in the manner described and shown herein.

While the apparatus, system and method herein described, and the form of apparatus for carrying this method into effect, constitute several illustrative embodiments of this invention, it is to be understood that the invention is not limited to this precise method and form of apparatus, and that changes may be made in either without departing from the scope of the inventions, which is defined in the appended claims.

What is claimed is:

1. A capless multiaxial screw fixation assembly comprising:
 a screw having a threaded portion and a screw head;
 an elongated member;
 a receiver having a bore for receiving said threaded portion and a first receiving channel for receiving said elongated member, said first receiving channel further comprising a locking channel in communication with said first receiving channel;

a compression member for situating in said bore, said compression member having a first end and a second end and further comprising:

a second receiving channel associated with said first end; and a seat area associated with said second end for receiving and engaging said screw head;

said elongated member causes said compression member to move toward said screw head in said bore to lock said elongated member to said screw when said elongated member is received in said first and second receiving channels and said receiver is rotated from an unlocked position to a locked position;

wherein when said receiver is rotated from said unlocked to said locked position, said elongated member and said compression member move in said bore so that they are closer to said screw head;

wherein said receiver comprises at least one camming surface that cooperates with an opposing surface for defining said locking channel said at least one camming surface facilitates camming said elongated member to urge said compression member to apply a compressive force against said screw head.

2. The capless multiaxial screw fixation assembly as recited in claim 1 wherein said receiver comprises a plurality of channels that capture said elongated member.

3. The capless multiaxial screw fixation assembly as recited in claim 2 wherein each of said plurality of channels defines an intermediate area for capturing said elongated member to facilitate adjusting a position of said elongated member before it is locked in said receiver.

4. The capless multiaxial screw fixation assembly as recited in claim 3 wherein said plurality of channels are defined by a first surface and a second surface, each of said plurality of channels having an intermediate step for defining said intermediate area.

5. The capless multiaxial screw fixation assembly as recited in claim 1 wherein said screw, receiver and compression member are preassembled.

6. The capless multiaxial screw fixation assembly as recited in claim 1 wherein said locking channel is a helical channel defined by at least one surface of said receiver.

7. The capless multiaxial screw fixation assembly as recited in claim 1 wherein said seat area is generally concave, said screw head having a curvature that generally complements said concave seat area.

8. The capless multiaxial screw fixation assembly as recited in claim 1 wherein said receiving channel comprises a first axis and said second receiving channel comprises a second axis, said second axis and said first axis being generally parallel when said receiver is in said unlocked position and generally perpendicular when said receiver is actuated to said locked position.

9. The capless multiaxial screw fixation assembly as recited in claim 1 wherein said receiving channel is generally perpendicular to an elongated member axis of said elongated member when said receiver is in said locked position.

10. The capless multiaxial screw fixation assembly as recited in claim 1 wherein said locking channel provides a bayonet connection between said elongated member and said screw.

11. The capless multiaxial screw fixation assembly as recited in claim 1 wherein said receiving channel is generally parallel along an axis of said receiver and said locking channel spirals about the axis of said receiver when moving in an axial direction.

12. The capless multiaxial screw fixation assembly as recited in claim 1 wherein said receiving channel extends from an end of said receiver in a direction that is generally parallel to an axis of said receiver and said locking channel extends in a direction that is generally not parallel to said axis of said receiver.

13. The capless multiaxial screw fixation assembly as recited in claim 1 wherein when said compression member is received in said bore and said receiving channel becomes generally aligned with said second receiving channel, said locking channel becomes situated at least partially around said compression member.

14. The capless multiaxial screw fixation assembly as recited in claim 1 wherein said receiver comprises a plurality of camming surfaces that cooperate with a plurality of opposing surfaces, respectively, to define said rocking channel, said plurality of camming surfaces camming against said elongated member to force said elongated member against said compression member which, in turn, applies a compressive force against said screw head when said receiver is rotated.

15. The capless multiaxial screw fixation assembly as recited in claim 14 wherein said locking channel comprises a first locking channel area and a second locking channel area, said receiver comprises a first camming surface generally opposed to a first opposing surface to define said first locking channel area and a second camming surface generally opposed to a second opposing surface to define said second locking channel area, said first and second camming surfaces camming against said elongated member to force said elongated member against said compression member which, in turn, applies a compressive force against said screw head when said receiver is rotated.

16. The capless multiaxial screw fixation assembly as recited in claim 15 wherein said compressive force is along an axis of said bore.

17. The capless multiaxial screw fixation assembly as recited in claim 15 wherein said receiver comprises an inner surface; said inner surface cooperating with said compression member to capture lock said screw head therebetween.

18. The capless multiaxial screw fixation assembly as recited in claim 1 wherein said locking channel comprises a lock member associated therewith for facilitating retaining said receiver in a locked position.

19. The capless multiaxial screw fixation assembly as recited in claim 18 wherein said lock member comprises a detent in said receiver and associated with said locking channel.

20. The capless multiaxial screw fixation assembly as recited in claim 19 wherein said lock member cooperates with an end wall of said locking channel to define a locking area at which said elongated member is locked when it is in said locked position.

21. The capless multiaxial screw fixation assembly as recited in claim 1 wherein said receiving channel lies in a first plane that is generally planar and said locking channel lies in a second plane that is non-planar.

22. The capless multiaxial screw fixation assembly as recited in claim 21 wherein said second plane spirals about an axis of said receiver.

23. The capless multiaxial screw fixation assembly as recited in claim 1 wherein said locking channel spirals about an axis of said receiver.

24. The capless multiaxial screw fixation assembly as recited in claim 1 wherein said screw head is generally spherical and said seat area is also generally spherical and dimensioned to receive and complement said screw head.

25. A spinal fixation assembly comprising:
a screw having a screw head;
an elongated member;
a receiver having a bore for receiving said screw; and
a compression member dimensioned to be received in said bore and having a first end for engagement with said elongated member and a second end for engagement with said screw head;
said receiver comprising a receiving channel in communication with locking channels;
said receiving channel receives said elongated member and cooperates with said looking channels to secure said elongated member to said screw when said receiver is rotated;
wherein when said receiver is rotated toward or into a locked position, said elongated member and said compression member move in said bore closer to said screw head until said compression member engages and locks against said screw head;
wherein said receiver comprises at least one camming surface that cooperates with an opposing surface for defining each of said locking channels, said at least one camming surface facilitates camming said elongated member to urge said compression member to apply a compressive force against said screw head when said receiver is rotated.

26. The spinal fixation system as recited in claim 25 wherein said receiver comprises a first engaging surface;
said first engaging surface engaging said elongated member and forcing it against said compression member which, in turn, engages said screw head with a compressive force when said receiver is rotated.

27. The spinal fixation system as recited in claim 26 wherein said locking channels comprise a first camming surface and a second camming surface, respectively, that engages said elongated member and forces it against said compression member until said elongated member becomes fixed relative to said screw.

28. The spinal fixation system as recited in claim 25 wherein said locking channel lies in a plane that is at predetermined angle relative to said receiving channel.

29. The spinal fixation system as recited in claim 28 wherein said predetermined angle is approximately 90 degrees.

30. The spinal fixation system as recited in claim 28 wherein said predetermined angle is an acute angle that extends toward a vertebrae when the screw is rotated.

31. A receiver assembly comprising a polyaxial screw having a screw head:
an elongated member;
a compression member;
a body having a bore for receiving said compression member said body having an open end for receiving said elongated member and a seat for receiving a portion of said polyaxial screw and a locking channel for receiving said elongated member and for locking it to the polyaxial screw when said receiver assembly is rotated; and
wherein when said receiver assembly is rotated, said elongated member forces said compression member from a first position to a second position in response thereto, said elongated member and said compression member moves closer to said screw head compared to when said elongated member is in said first position;
wherein said body comprises at least one camming surface that cooperates with an opposing surface for defining said locking channel, said at least one camming surface facilitates camming said elongated member to urge said compression member to apply a compressive force against said screw head so that said portion of said polyaxial screw engages said seat.

32. The receiver assembly as recited in claim 31 wherein said locking channel defines a bayonet connection channel.

33. The receiver assembly as recited in claim 32 wherein said connection channel comprises a plurality of channels that cooperate to define said bayonet connection channel.

34. The receiver assembly as recited in claim 33 wherein said plurality of channels spiral about an axis of said receiver assembly.

35. A capless multiaxial screw comprising:
an elongated member;
a screw having a threaded portion and a screw head; and
a receiver having a bore for receiving said threaded portion and a receiving channel for receiving said elongated member, said receiver further comprising a locking channel in communication with said receiving channel;
said receiver rocking said elongated member to said screw when said elongated member is received in said receiving channel and said receiver is rotated from an unlocked position to a locked position;
wherein when said receiver is rotated from said unlocked to said locked position, said elongated member moves along an axis of said bore and becomes closer to said screw head;
wherein said receiver comprises at least one camming surface that cooperates with an opposing surface for defining said locking channel, said at least one camming surface facilitates camming said elongated member to urge a compression member to apply a compressive force against said screw head which causes said elongated member and said screw head to become locked in said receiver.

36. The capless multiaxial screw as recited in claim 35 wherein said receiver comprises a plurality of channels that capture said elongated member.

37. The capless multiaxial screw as recited in claim 36 wherein each of said plurality of channels defines an intermediate area for capturing said elongated member to facilitate adjusting a position of said elongated member before it is locked in said receiver.

38. The capless multiaxial screw as recited in claim 37 wherein said plurality of channels are defined by a first surface and a second surface, each of said plurality of channels having an intermediate step for defining said intermediate area.

39. The capless multiaxial screw as recited in claim 38 wherein at least one of said first and second surfaces is not planar.

40. The capless multiaxial screw as recited in claim 35 wherein said locking channel is a helical channel defined by at least one surface of said receiver.

41. The capless multiaxial screw as recited in claim 35 wherein said capless multiaxial screw further comprises a compression member for situating in said bore, said compression member comprising a generally concave seat, said screw head having a curvature that generally complements said generally concave seat.

42. The capless multiaxial screw as recited in claim 35 wherein said receiving channel comprises a first axis, an axis of said elongated member being generally parallel to said first axis when said elongated member is in said unlocked position and generally perpendicular when said receiver is actuated to said locked position.

43. The capless multiaxial screw as recited in claim 35 wherein when said receiver is rotated, said receiver moves said elongated member from a first position to a second position in response thereto, such that when said receiver is in said second position, said elongated member is locked to said screw head.

44. The capless multiaxial screw as recited in claim 35 wherein when said receiver is rotated, said receiver moves said elongated member from a first position, through an intermediate position, to a second position.

45. The capless multiaxial screw as recited in claim 43 wherein said first position corresponds to said unlocked position and said second position corresponds to said locked position.

46. The capless multiaxial screw as recited in claim 35 wherein said receiving channel is generally perpendicular to an elongated member axis of said elongated member when said receiver is in said locked position.

47. The capless multiaxial screw as recited in claim 35 wherein said locking channel provides a bayonet connection.

48. The capless multiaxial screw as recited in claim 35 wherein said receiving channel is generally parallel along an axis of said receiver and said locking channel spirals about said axis of said receiver when moving in an axial direction.

49. The capless multiaxial screw as recited in claim 35 wherein said receiving channel extends from an end of said receiver in a direction that is generally parallel to an axis of said receiver and said locking channel extends in a direction that is generally not parallel to said axis of said receiver.

50. The capless multiaxial screw as recited in claim 35 wherein said receiver comprises a plurality of camming surfaces that cooperates with a plurality of opposing surfaces, respectively, for defining said locking channel, said plurality of camming surfaces compressing said elongated member against said screw head.

51. The capless multiaxial screw as recited in claim 35 wherein said receiver comprises a plurality of camming surfaces that cooperate with a plurality of opposing surfaces, respectively, to define said locking channel, said a plurality of camming surfaces for camming against said elongated member to lock said receiver to said screw.

52. The capless multiaxial screw as recited in claim 51 wherein said locking channel comprises a first locking channel area and a second locking channel area, said receiver comprises a first camming surface generally opposed to a first opposing surface to define said first looking channel area and a second camming surface generally opposed to a second opposing surface to define said second locking channel area, said first and second camming surfaces camming against said elongated member to force said elongated member against said compression member which, in turn, applies a compressive force against said screw head when said receiver is rotated.

53. The capless multiaxial screw as recited in claim 35 wherein said locking channel comprises a lock member associated therewith for facilitating retaining said receiver in a locked position.

54. The capless multiaxial screw as recited in claim 53 wherein said lock member comprises a detent in said receiver and associated with said locking channel.

55. The capless multiaxial screw as recited in claim 54 wherein said lock member cooperates with an end wall of said locking channel to define a locking area at which said receiving member is locked when it is in said locked position.

56. The capless multiaxial screw as recited in claim 35 wherein said receiving channel lies in a first plane that is generally planar and said locking channel lies in a second plane that is non-planar.

57. The capless multiaxial screw as recited in claim 56 wherein said second plane spirals about an axis of said receiver.

58. The capless multiaxial screw as recited in claim 35 wherein said locking channel spirals about an axis of said receiver.

59. The capless multiaxial screw as recited in claim 35 wherein said receiver comprises a seat, said screw head is being generally spherical and said seat is also generally spherical and dimensioned to receive and complement said screw head.

* * * * *

UNITED STATES PATENT AND TRADEMARK OFFICE
CERTIFICATE OF CORRECTION

| | | |
|---|---|---|
| PATENT NO. | : 7,717,943 B2 | |
| APPLICATION NO. | : 11/193523 | |
| DATED | : May 18, 2010 | |
| INVENTOR(S) | : David Louis Kirschman | |

It is certified that error appears in the above-identified patent and that said Letters Patent is hereby corrected as shown below:

In Column 9, Line 2, after the word "plurality", please insert -- of --.

In Column 10, Line 53, please delete "In" and insert -- in -- therefor.

In Column 12, Line 23, please delete "FIGS." and insert -- FIG. -- therefor.

In Column 13, Line 23, after the word "channel", please insert -- , --.

In Column 14, Line 19, please delete "rocking" and insert -- locking -- therefor.

In Column 15, Line 14, please delete "looking" and insert -- locking -- therefor.

In Column 15, Line 42, after the word "at", please insert -- a --.

In Column 15, Lines 51 and 52 please delete "31. A receiver assembly comprising a polyaxial screw having a screw head:" and insert the following in their place:

-- 31. A receiver assembly comprising:

a polyaxial screw having a screw head; --.

In Column 15, Line 56, please insert -- , -- before said body.

In Column 16, Line 23, please delete "rocking" and insert -- locking -- therefor.

In Column 16, Line 60, please delete "said capless multiaxial screw further comprises a compression member for situating in said bore,".

In Column 16, Line 62, please delete "comprising" and insert -- comprises -- therefor.

Signed and Sealed this
Twenty-fifth Day of October, 2011

David J. Kappos
*Director of the United States Patent and Trademark Office*

In Column 18, Line 7, please delete "looking" and insert -- locking -- therefor.